(12) United States Patent
Lohse et al.

(10) Patent No.: US 8,796,428 B2
(45) Date of Patent: Aug. 5, 2014

(54) ERK1/2 POSPHORYLATION SITE SPECIFIC ANTIBODY

(75) Inventors: Martin J. Lohse, Wuertzburg (DE); Kristina Lorenz, Wuerzburg (DE)

(73) Assignee: Julius-Maximilians-Universitaet Wuerzburg, Wuerzburg (DE)

( * ) Notice: Subject to any disclaimer, the term of this patent is extended or adjusted under 35 U.S.C. 154(b) by 272 days.

(21) Appl. No.: 13/130,495

(22) PCT Filed: Nov. 26, 2009

(86) PCT No.: PCT/EP2009/065935
§ 371 (c)(1),
(2), (4) Date: Jul. 12, 2011

(87) PCT Pub. No.: WO2010/060972
PCT Pub. Date: Jun. 3, 2010

(65) Prior Publication Data
US 2011/0274694 A1    Nov. 10, 2011

(30) Foreign Application Priority Data

Nov. 26, 2008   (EP) ..................................... 08020518

(51) Int. Cl.
*C07K 16/40* (2006.01)
*C07K 16/00* (2006.01)
*C12N 5/07* (2010.01)
*G01N 33/53* (2006.01)

(52) U.S. Cl.
USPC ............... 530/388.26; 530/388.1; 530/387.9; 530/387.1; 435/326; 435/7.1

(58) Field of Classification Search
CPC . C12Q 1/485; G01N 33/573; G01N 33/6842; C07K 16/44; A61K 2300/00
See application file for complete search history.

(56) References Cited

FOREIGN PATENT DOCUMENTS

| JP | 409005632 A | * | 1/1996 |
|---|---|---|---|
| WO | 01/07638 | | 2/2001 |
| WO | 2007/014033 | | 2/2007 |
| WO | 2007/028430 | | 3/2007 |

OTHER PUBLICATIONS

English translation of JP408005632A.*
Anonymous, (2010) "Phosphorylation Site Page: Thr188-ERK2 (mouse)" 2010, XP002569067. Retrieved from the Internet: http://www.phosphosite.org/siteAction.do?id=3949253.
Anonymous, (2010) "Phosphorylation Site Page Thr207-ERK1 (human)" 2010, XP002569068. Retrieved from the Internet: http://www.phosphosite.org/siteAction.do?id=3949244.
Bogoyevitch, M. A, et al. (1996) "The Role of Protein Kinases in Adaptional Growth of the Heart" Int. J. Cell. Biol. 28, 1-12.
Brown, J. H. et al. (1997) "Pathways and Roadblocks in Muscarinic Receptor-Mediated Growth Regulation" Life Sciences 60, 1077-1084.
Brunet, A. et al. (1999) "Nuclear Translocation of p42/p44 Mitogen-activated Protein Kinase is Required for Growth Factor-Induced Gene Expression and Cell Cycle Entry." EMBO J. 18, 664-674.
Database WPI Week 199641 Thomson Scientific, London, GB; An 1996-405837, XP002569066-& JP 08 005632 A (Sumito Chem Co Ltd) Jan. 12, 1996, p. 3, col. 1, sequence (15).
Garrington, T. P. et al. (1999) "Organization and Regulation of Mitogen-activated Protein Kinase Signaling Pathways" Curr. Opin. Cell. Biol. 11, 211-218.
Khokhlatchev, A. V. et al. (1998) "Phosphorylation of the MAP Kinase ERK2 Promotes its Homodimerization and Nuclear Translocation" Cell 93, 605-615.
Lorenz, K., et al. (2003) "Protein Kinase C Switches the Raf Kinase Inhibitor from Raf-1 to GRK-2" Nature 426, 574-579.
Lorenz, K. et al. (2009) "A New Type of ERK1/2 Autophosphorylation Causes Cardiac Hypertrophy" Nature Medicine 15, 1, 75-83.
Lorenz, K. et al. (2009) "Cardiac Hypertrophy: Targeting Raf/MEK/ERK!/2-signaling" International Journal of Biochemistry and Cell Biology 41, 1, 2351-2355.
Mansour, S. J. et al. (1994) "Transformation of Mammalian Cells by Constitutively Active MAP Kinase Kinase" Science 265, 966-970.
Muslin, A. J. (2005) "Role of Raf Proteins in Cardiac Hypertrophy and Cardiomyocyte Survival" Trands Cardiovasc. Med. 15, 225-229.
Slupsky, J. R. et al. (1999) "Binding of Gβγ Subunits to cRaf1 Downregulates G-protein-coupled Receptor Signalling" Curr. Biol. 9, 971-974.
Sugden, P. H. et al. "Cellular Mechanisms of Cardiac Hypertrophy" J. Mol. Med. 76, 725-746.
International Search Report received in PCT/EP2009/065935. Mailed Feb. 26, 2010.
Written Opinion of the International Searching Authority received in PCT/EP2009/065935. Mailed Feb. 26, 2010.

* cited by examiner

*Primary Examiner* — Sharon Wen
(74) *Attorney, Agent, or Firm* — Suzannah K. Sundby, Esq.; Smith, Gambrell & Russell, LLP

(57) ABSTRACT

The invention relates to an antibody specific to Erk1/2 phosphorylated at Thr188 and a method for producing the same. The invention also relates to an in vitro method for determining the presence of phosphorylated Erk1/2 in a sample using the antibody of the invention. Therefore, the invention also comprises an assay for diagnosing a heart disease in vitro comprising the antibody of the invention and certain uses of the antibody. Moreover the invention relates to a peptide used to produce the antibody.

14 Claims, 10 Drawing Sheets

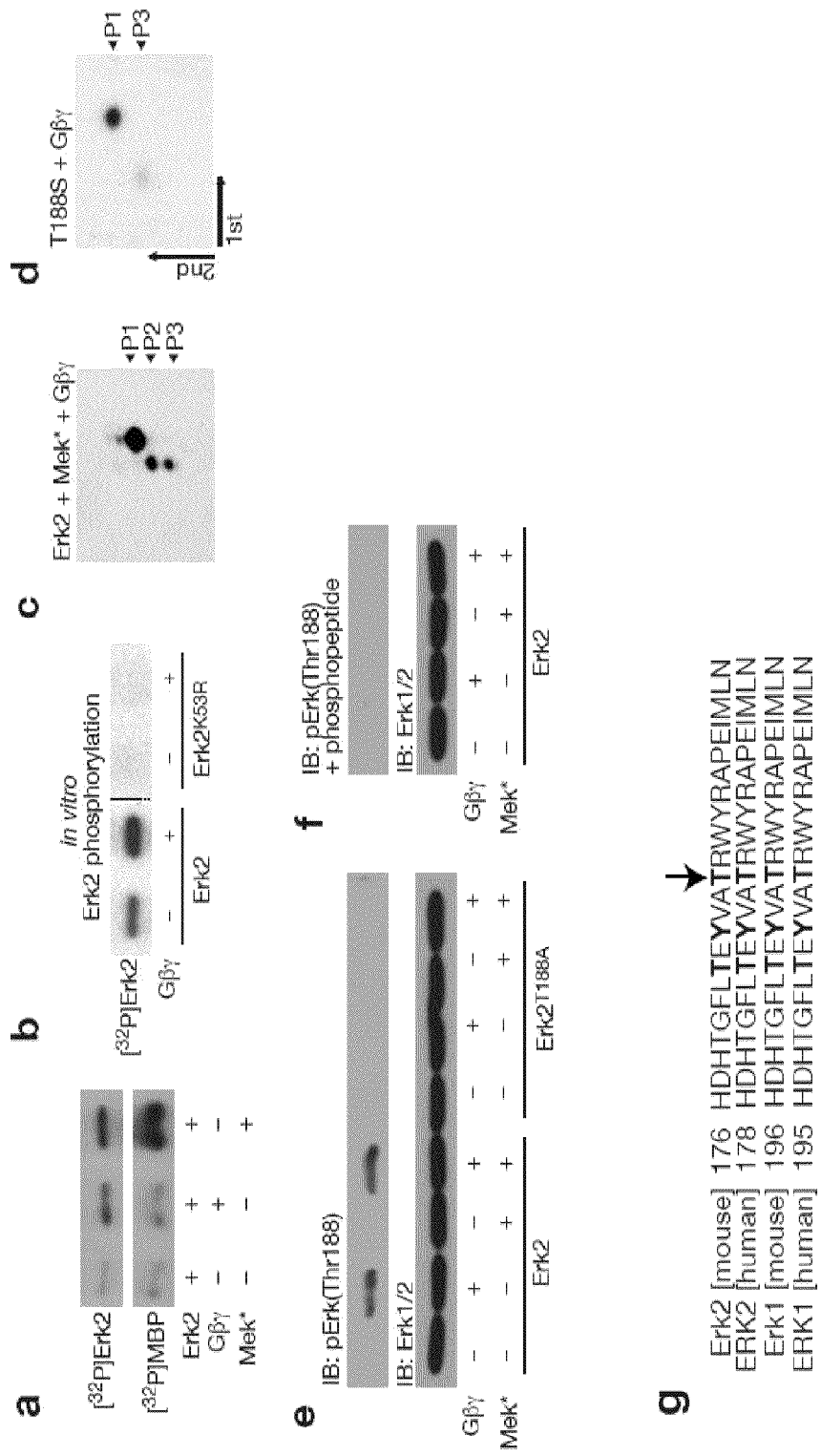
Figure 1.1

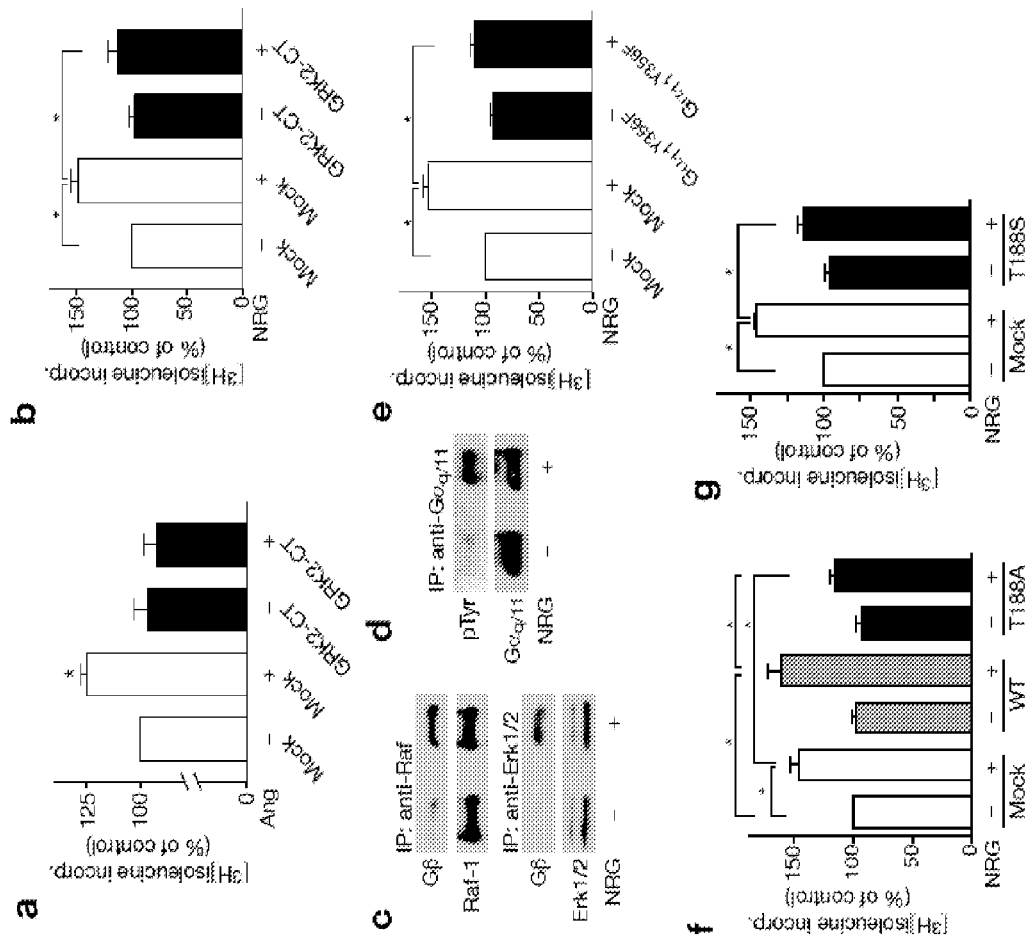
Figure 3.1

ERK1/2 POSPHORYLATION SITE SPECIFIC ANTIBODY

REFERENCE TO A SEQUENCE LISTING SUBMITTED VIA EFS-WEB

The content of the ASCII text file of the sequence listing named "20110520_034267_004_seqtxt" which is 15.1 KB in size was created on 20 May 2011 and electronically submitted via EFS-Web herewith the application is incorporated herein by reference in its entirety.

FIELD OF THE INVENTION

The present invention relates to an antibody specific to phosphorylated Erk1/2 and a method for producing the same. The invention also relates to an in vitro method for determining the presence of phosphorylated Erk1 and/or Erk2 (Erk1/2) in a sample, an assay for diagnosing a heart disease and certain uses of the antibody. Moreover the invention relates to peptides for the production of the antibody.

BACKGROUND OF THE INVENTION

Cardiac hypertrophy occurs in response to increased mechanical load and through the action of several hormones and mediators (Sugden and Clerk, 1998). It involves enhanced protein synthesis, cardiomyocyte growth and cytoskeletal reorganization, and is often associated with interstitial fibrosis (Sugden and Clerk, 1998). The mitogen-activated protein kinase (MAPK)-cascade, consisting of Raf1 (rapid growing fibro sarcoma), MEK1/2 (mitogen-activated protein kinase kinases) and ERK1/2 (extracellular signal-regulated kinases), plays a prominent role in cardiac hypertrophy (Sugden and Clerk, 1998).

Activation of the cascade begins with activation of Raf1, which leads to sequential phosphorylation and activation of MEK1/2 and then ERK1/2. MEK1/2 activates ERK1/2 by dual phosphorylation of the threonine- and tyrosine-residues in the TEY-motif of the activation loop (183-185 in mouse ERK2). ERK2 can autophosphorylate at Tyr185, but phosphorylation of both Thr183 and Tyr185 by MEK1/2 is required for full activation (Muslin, 2005). However, the mechanisms regulating the MAPK cascade and thereby leading to cardiac hypertrophy are largely unknown.

SUMMARY OF THE INVENTION

In a first aspect, the present invention relates to an antibody specific to SEQ ID NO: 1 of Erk1 or Erk2, wherein the threonine (Thr) at position 8 of the sequence is phosphorylated.

In a further aspect the invention relates to a peptide consisting of SEQ ID NO: 1.

In a further aspect the invention relates to a nucleic acid encoding SEQ ID NO: 1.

In a further aspect the invention relates to a non-human host producing an antibody specific to SEQ ID NO: 1 of Erk1 or Erk2, wherein the Thr at position 8 of the sequence is phosphorylated.

In a further aspect the invention relates to an in vitro method for determining the presence of phosphorylated Erk1 and/or Erk2 (Erk1/2) in a sample, comprising the steps of providing an antibody specific to SEQ ID NO: 1 of Erk1 or Erk2, wherein the Thr at position 8 of the sequence is phosphorylated, incubating the sample with the antibody in vitro, detecting the antibody bound to the sample, wherein binding of the antibody to the sample indicates the presence of phosphorylated Erk1/2 in the sample.

In a further aspect the invention relates to a method for producing an antibody specific to SEQ ID NO: 1 of Erk1 or Erk2, wherein the Thr at position 8 of the sequence is phosphorylated, comprising the steps of providing a peptide of SEQ ID NO: 1, producing an antiserum against the peptide, subjecting the antiserum to the peptide of SEQ ID NO: 1 for extracting a peptide-specific antibody for Erk1/2 and/or to the peptide of SEQ ID NO: 1 in which the Thr at position 8 of the sequence is phosphorylated, for isolating a phospho-specific antibody for Erk1/2.

In a further aspect the invention relates to a kit for determining the presence of phosphorylated Erk1/2 in a sample, comprising an antibody specific to SEQ ID NO: 1 of Erk1 or Erk2, wherein the Thr at position 8 of the sequence is phosphorylated.

In a further aspect the invention relates to an assay for diagnosing a heart disease, comprising an antibody specific to SEQ ID NO: 1 of Erk1 or Erk2, wherein the Thr at position 8 of the sequence is phosphorylated, and wherein the phosphorylated Thr indicates a heart disease, preferably cardiac hypertrophy.

In a further aspect the invention relates to the use of an antibody specific to SEQ ID NO: 1 of Erk1 or Erk2, wherein the Thr at position 8 of the sequence is phosphorylated for manufacturing an assay for detecting the presence and/or the amount of phosphorylated Erk1/2 in a sample.

In a further aspect the invention relates to the use of an antibody specific to SEQ ID NO: 1 of Erk1 or Erk2, wherein the Thr at position 8 of the sequence is phosphorylated for manufacturing an assay for analyzing the hypertrophic stimulus of a patient.

In a further aspect the invention relates to the use of an antibody specific to SEQ ID NO: 1 of Erk1 or Erk2, wherein the Thr at position 8 of the sequence is phosphorylated for manufacturing an assay for detecting Erk1/2 signaling activity in tissue, preferably in heart or cancer tissue.

In a further aspect the invention relates to the use of an antibody specific to SEQ ID NO: 1 of Erk1 or Erk2, wherein the Thr at position 8 of the sequence is phosphorylated for manufacturing a pharmaceutical composition for the treatment of a disease selected from the group consisting of heart diseases, in particular heart failure, cardiac hypertrophy, interstitial fibrosis, cardiac dysfunction, aortic valve stenosis, cancer, in particular cancer of epithelial origin, colorectal adenocarcinoma, colon adenocarcinoma, lung adenocarcinoma, basal lung squamous cell carcinoma and small cell lung carcinoma.

In a further aspect, the invention relates to the use of SEQ ID NO: 1 in which the Thr at position 8 of the sequence is phosphorylated for triggering hypertrophic phenotypes in cells in vitro.

In a further aspect, the invention relates to the use of SEQ ID NO: 1 for producing an antibody specific to SEQ ID NO: 1 of Erk1 or Erk2, wherein the Thr at position 8 of the sequence is phosphorylated.

BRIEF DESCRIPTION OF THE DRAWINGS

FIG. 1.1 shows that purified Gβγ induce autophosphorylation of purified Erk2 at Thr188.

FIG. 3.1 shows neuregulin-induced cellular hypertrophy involving Gβγ.

DETAILED DESCRIPTION OF THE INVENTION

In a first aspect, the invention relates to an antibody specific to SEQ ID NO: 1 of Erk1 or Erk2, wherein the threonine (Thr) at position 8 of the sequence is phosphorylated.

Figure 1:
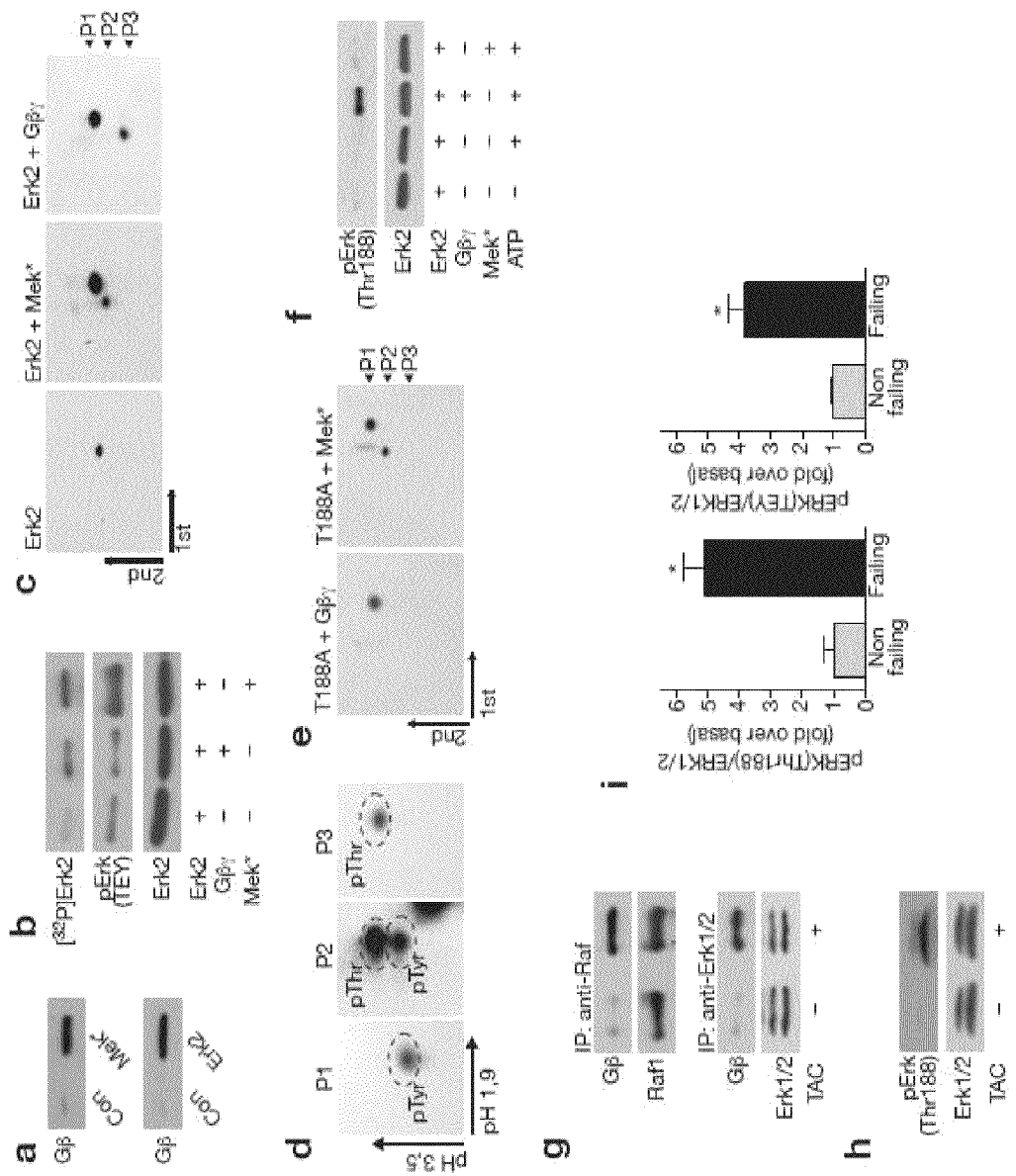
FIG. 1 shows Gβγ-induced autophosphorylation of Erk2 at Thr188.

The proteins Erk1 mouse (SEQ ID NO: 7) and Erk2 mouse (SEQ ID NO: 8), also known as extracellular signal-regulated kinases, act in a signaling cascade which regulates various cellular processes such as proliferation, differentiation, and cell cycle progression. Both proteins are highly homologous, especially in their kinase domain (amino acid 22-318 of Erk2). This homology is even conserved between species, e.g. the homology of SEQ ID NO: 1 of Erk1 and 2 is absolute identical between mouse and human (Erk1 human: SEQ ID NO: 9, Erk2 human: SEQ ID NO: 10) (FIG. 1.1 g). Therefore, Erk1 and/or Erk2 are henceforth referred to as Erk1/2, wherein the numbering of the amino acids refers to Erk2, unless indicated otherwise.

Erk1/2 is activated by phosphorylation, mediated by MEK1/2, on the amino acids threonine (Thr)183 and tyrosine (Tyr)185. The inventors, however, found that in addition to MEK1/2, also G-protein-βγ-subunits interact with Erk1/2, causing a phosphorylation of Erk1/2 as well (FIG. 1 a-c). Even more surprisingly the inventors could show that the phosphorylation of Erk1/2 induced by Gβγ did not occur at the known, thus canonical, phosphorylation sites of Erk1/2 (Thr183 and Tyr185) (FIG. 1.1 b). They identified a new phosphorylation site, Thr at position 8 of SEQ ID NO: 1 of Erk/2, corresponding to Thr208 of Erk1 and Thr188 of Erk2, respectively (FIGS. 1 e, f, FIGS. 1.1 e, g.). The identification of this, so far unknown, phosphorylation site enabled the inventors to generate an antibody which is specific to SEQ ID NO: 1 of Erk1 or Erk2, wherein the Thr at position 8 of the sequence is phosphorylated. This antibody allows to distinguish Erk1/2 phosphorylated at Thr183/Thy185 from Erk1/2 phosphorylated at Thr188. This finding provides an important tool, since the different phosphorylations are induced by distinct up-stream signaling (Results 1.3, FIGS. 2 a, c, d, FIGS. 3.1 a, d) and influence the functions of Erk1/2 within the cell (Results 1.8, 9, FIG. 5) and in diseases as e.g. cardiac hypertrophy or cancer (Results 1.5, 1.11, FIGS. 7, 8).

In a preferred embodiment, the antibody is monoclonal or polyclonal. Monoclonal antibodies are monospecific antibodies produced by one type of immune cell, such that all antibodies generated from the clone of this cell recognize the same epitope of the antigen. Their detection is particularly specific, since they rarely bind false targets. Moreover monoclonal antibodies also share the same isotype, reducing background signal from unspecific binding when the antibody is detected, e.g. by secondary antibodies. Polyclonal antibodies in contrast, are a mixture of immunoglobulin molecules specific to one antigen, however recognizing different epitopes of the same. Generally they give stronger signals than monoclonal antibodies reducing the effort needed for detection, e.g. amplification of signals.

In a preferred embodiment the antibody binds to SEQ ID NO: 1, recognizing the structure of the Erk1/2 molecule which is derived from the amino acids of SEQ ID NO: 1 of Erk1/2.

In a preferred embodiment, the antibody specifically binds to the phosphorylated Thr, which is more preferred Thr[208] of Erk1 or Thr[188] of Erk2.

In a preferred embodiment, the antibody is supplemented with the peptide of SEQ ID NO: 1. This is to ensure the elimination of residual non-phosphospecific antibodies to improve binding specificity and to reduce background signal. This is particularly important to precisely distinguish between Erk1/2 phosphorylated at the canonical phosphorylation site and Erk1/2 phosphorylated at Thr188.

In a further aspect, the invention relates to a peptide consisting of SEQ ID NO: 1. This peptide represents one part of the kinase domain which is conserved between Erk1 and Erk2. namely amino acids 176-199 of mouse Erk2, 178-201 of human Erk2, 196-219 of mouse Erk1 and 195-218 of human Erk1 (FIG. 1.1 g). Since the peptide includes the new phosphorylation site (Thr at position 8 of SEQ ID NO: 1) the inventors used it for generating the antibody of the invention.

In a preferred embodiment, the Thr at position 8 of the sequence (SEQ ID NO: 1) is phosphorylated, such that the peptide can e.g. be used for purifying the antibody of the invention.

In a further aspect, the invention relates to a nucleic acid encoding the peptide of SEQ ID NO: 1 preferably to SEQ ID NO: 3. This nucleic acid is used to produce the peptide in transgenic organism, as e.g. bacteria which are than used for antibody production. The production of small peptides in host cells is preferred, since it is less costly than an artificial synthesis.

In a further aspect, the invention relates to a non-human host producing an antibody specific to SEQ ID NO: 1 of Erk1 or Erk2, wherein the Thr at position 8 of the sequence is phosphorylated. In a preferred embodiment the host is a non-human mammal selected from the group consisting of donkey, goat, sheep, guinea pig, hamster, rabbit, rat and mouse or a non-human cell line, preferably a hybridoma cell line.

For example, for generating polyclonal antibodies suitable hosts are rabbit, guinea pig and goat, whereas monoclonal antibodies are preferably generated using mouse or rat hybridoma cell lines. Recently, rabbit monoclonal antibodies have been developed combining the advantages of rabbit-derived, which can be detected by secondary antibodies without intense background signal, and monoclonal antibodies exhibiting great specificity.

In a further aspect, the invention relates to an in vitro method for determining the presence of phosphorylated Erk1 and/or Erk2 (Erk1/2) in a sample, comprising the steps of providing an antibody specific to SEQ ID NO: 1 of Erk1 or Erk2, wherein the Thr at position 8 of the sequence is phosphorylated, incubating the sample with the antibody in vitro, detecting the antibody bound to the sample, wherein binding of the antibody to the sample indicates the presence of phosphorylated Erk1/2 in the sample.

Figure 2:
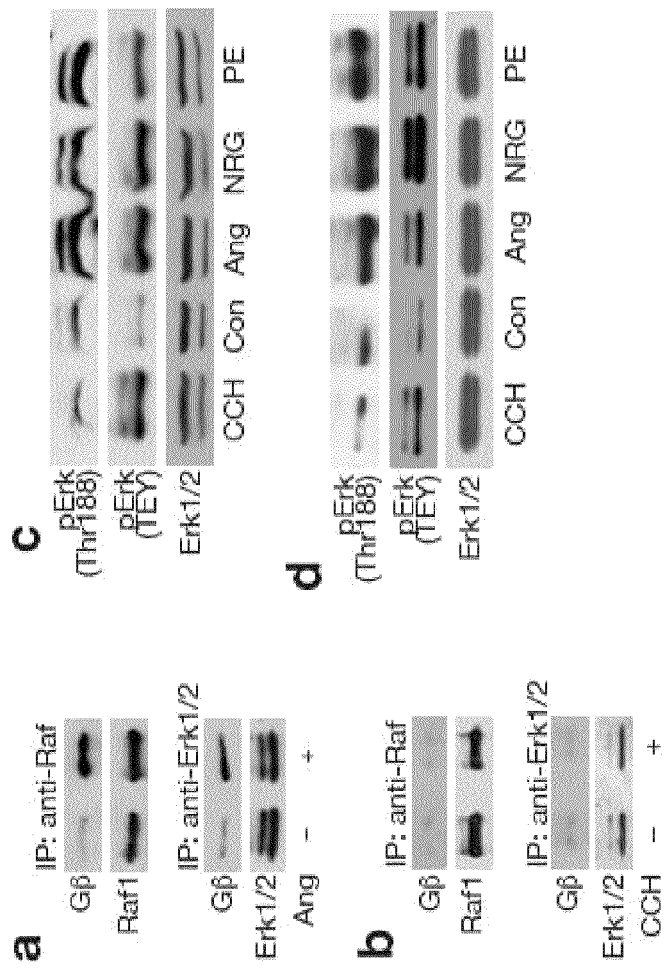
FIG. 2 shows that hypertrophic stimuli induce a stable interaction of Gβγ with Raf1 and Erk1/2 and induce Thr188-phosphorylation of Erk1/2.
Figure 3:
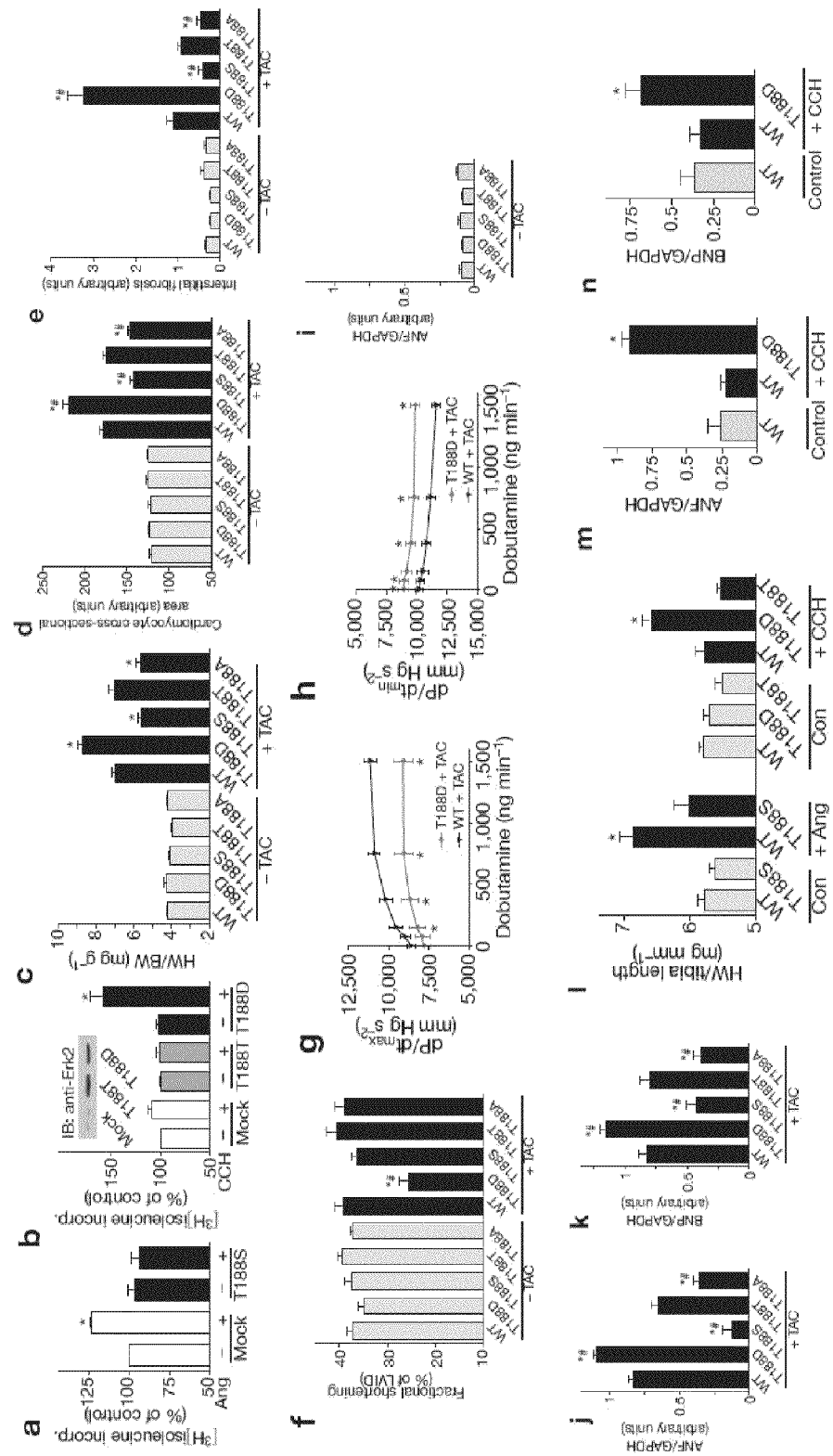
FIG. 3 shows that Thr188-phosphorylation is critical for hypertrophy of neonatal rat cardiomyocytes (NRCMs) and cardiac hypertrophy.
Figure 5:
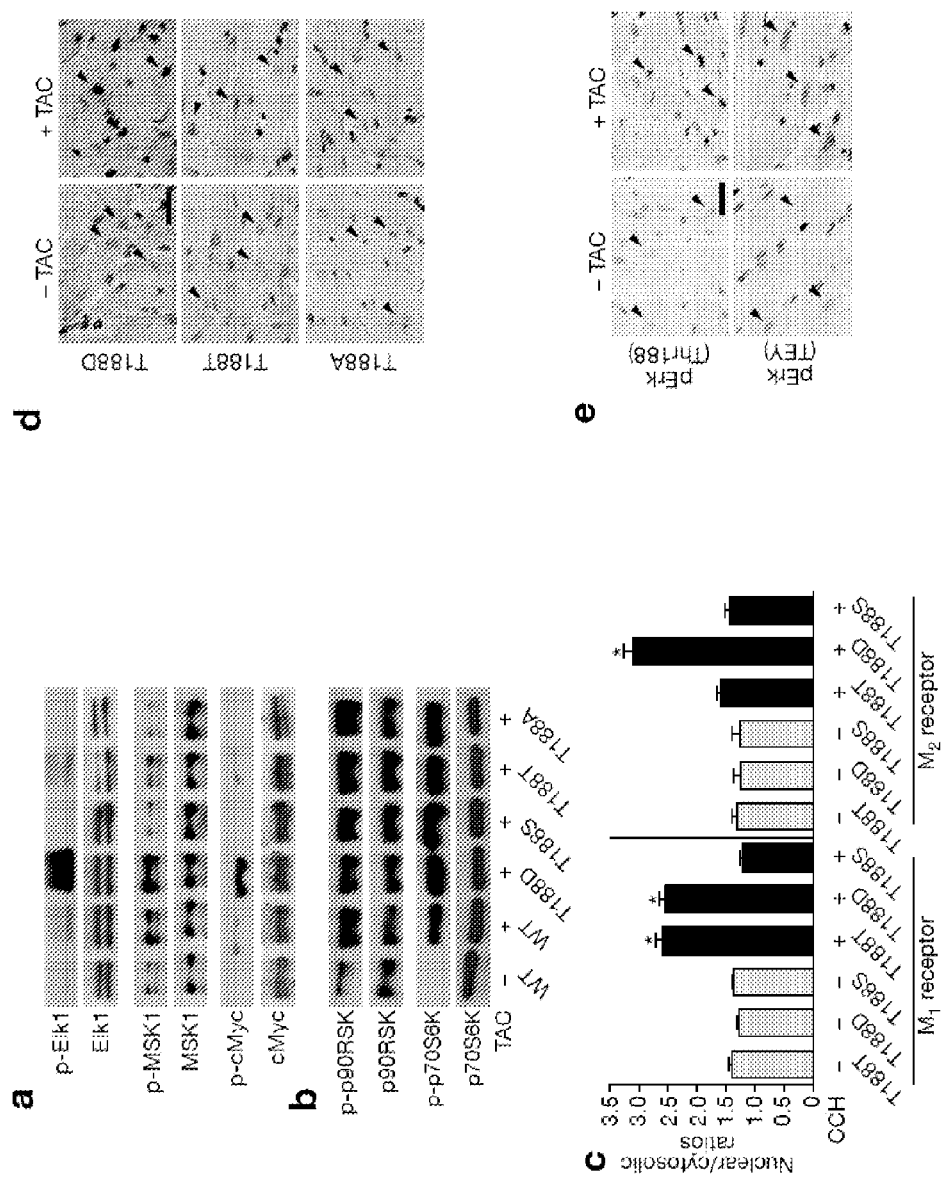
FIG. 5 shows that Thr188-phosphorylation promotes nuclear localization of Erk1/2.

The inventors found that Erk1/2 phosphorylated at Thr188 exerts other cellular functions than Erk1/2 phosphorylated at the canonical phosphorylation sites Thr183/Tyr185 (Results 1.8, 1.9, FIG. 3, FIGS. 5 a, c, e). In addition, Thr188 phosphorylated Erk1/2 has specific functions in cardiac hypertrophy (Results 1.3, 1.5, 1.10, FIGS. 2, c, d, FIGS. 3.1, a, b, FIG.

Figure 8:
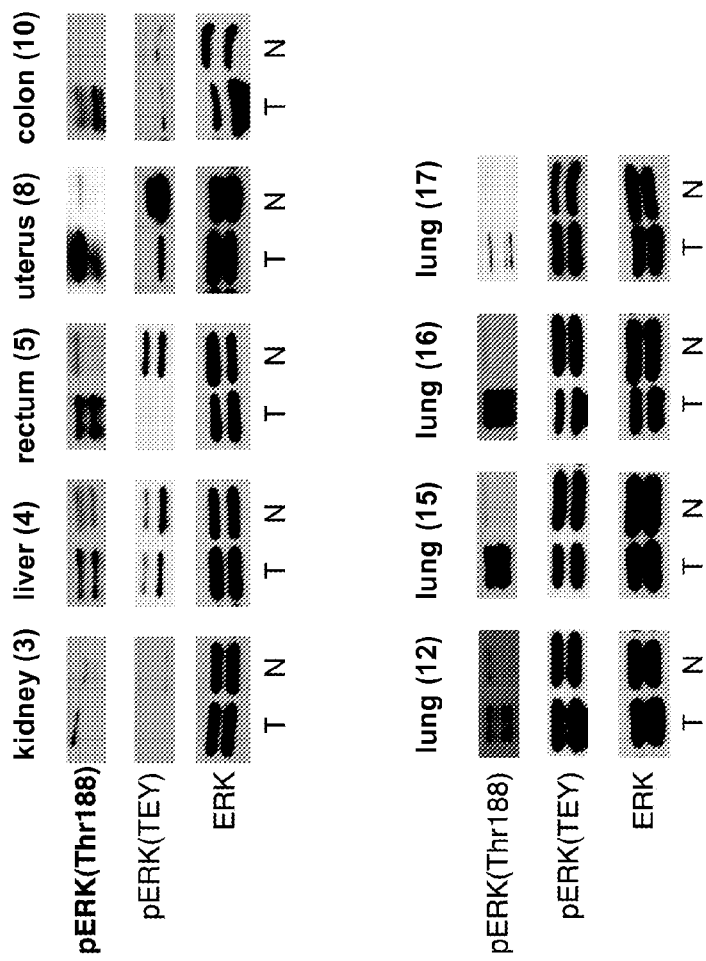
FIG. 8 Analysis of Thr188-phosphorylation as a marker of epithelia derived cancer.

7) and is specifically expressed in cancer (Results 1.11, FIG. 8). Therefore a method for determining the presence of Erk1/2 phosphorylated at Thr188, by using the antibody of the invention, provides an important in vitro tool for analysis and diagnosis. By detecting the presence of phosphorylated Erk1/2, additional information is provided which can improve the decision for a particular therapy.

In a preferred embodiment, the amount of antibody bound to the sample indicates the amount of Erk1/2 present in the sample, enabling the analyst to estimate the overall activation of the Gly-protein induced pathway (Results 1.6).

In a preferred embodiment, the sample is derived from a patient, preferably from a patient suffering from heart disease or cancer. Since the phosphorylated Erk1/2 is particularly high expressed in the tissue of failing hearts and in cancer tissue (Results 1.10, 1.11, FIG. 8), tissue from these groups of patients is preferred for the method of the invention.

The term "heart disease" as used herein, particularly refers to heart diseases caused or accompanied by cardiac hypertrophy, increased wall thickness and heart weight, increased cardiac myocyte growth, instial fibrosis, aortic valve stenosis and cardiac dysfunction. The term "cancer" as used herein, particularly refers to cancer derived from epithelial cells as e.g. colorectal adenocarcinoma, colon adenocarcinoma, lung adenocarcinoma, basal lung squamous cell carcinoma and small cell lung carcinoma.

In a further aspect, the invention relates to a method for producing an antibody specific to SEQ ID NO: 1 of Erk1 or Erk2, wherein the Thr at position 8 of the sequence is phosphorylated, comprising the steps of providing a peptide of SEQ ID NO: 1, producing an antiserum against the peptide, subjecting the antiserum to the peptide of SEQ ID NO: 1 for extracting a peptide-specific antibody for Erk1/2 and/or to the peptide of SEQ ID NO: 1 in which the Thr at position 8 of the sequence is phosphorylated, for isolating a phospho-specific antibody for Erk1/2.

The production of antibodies relies on the in vivo humoral response, wherein the immune system can be manipulated to increase the response by modifying either the antigen or the host. Most naturally occurring or synthetic compounds can be used as immunogens. Peptides might be conjugated to a carrier protein, e.g. bovine serum albumin or keyhole limpet hemocyanin to improve their immunogenity, or may be administered with an adjuvant to ensure a high quality/quantity response. Adjuvants are non-specific stimulators of the immune response, which allow the use of smaller doses of antigen.

The term "antiserum" as used herein, refers to any kind of substance which is suited for comprising an antibody, including the substances in which an antibody is usually produced, harvested or stored, e.g. blood, blood serum, immune serum, supernatant of cell cultures or storage buffer.

Depending on the nature of the antibody, polyclonal or monoclonal, an antiserum can be produced by injecting the peptide of SEQ ID NO: 1 into a non-human animal host, e.g. into a rabbit or a mouse. For producing polyclonal antibodies repeated immunization is induced by administering the peptide to the animal, at intervals of several weeks, to stimulate specific B cells to produce large amounts of the antibody. For producing monoclonal antibodies, following immunization, all antibody forming cells, e.g. mature B cells, are removed and fused with immortal tumor cells to become hybridomas. They are then screened for antibody production and cloned by isolation and cultivated using tissue culture or within mice to produce ascites fluid. The antibody secreted by the cells is harvested, e.g. as tissue culture supernatant.

To enrich the amount of antibody in the antiserum, affinity purification can be used, e.g. by subjecting the antiserum to a CNBr-sepharose column containing the peptide of SEQ ID NO: 1 and subsequently, or directly, subjecting the antiserum to a column containing the immunogenic, peptide of SEQ ID NO: 1 (FLTEYVA-(p)T-RWYRAPE) phosphorylated at Thr at position 8 and conjugated to *Limulus polyphemus* hemocyanine, for isolating the phosphospecific antibodies.

In a preferred embodiment the method further comprises the step of supplementing the phospho-specific antibody with the peptide of SEQ ID NO: 1, to ensure elimination of residual non-phosphospecific antibodies. This is to ensure the elimination of residual non-phosphospecific antibodies which otherwise reduce binding specificity and increase background signal. This is particularly important to precisely distinguish between Erk1/2 phosphorylated at the canonical phosphorylation site and Erk1/2 phosphorylated at Thr188.

In a further aspect, the invention relates to a kit for determining the presence of phosphorylated Erk1/2 in a sample, comprising an antibody specific to SEQ ID NO: 1 of Erk1 or Erk2, wherein the Thr at position 8 of the sequence is phosphorylated. This kit provides an equipment, which can be easily handled and is particularly suited for the use in hospitals or medical practice.

In a further aspect, the invention relates to an assay for diagnosing a heart disease, comprising an antibody specific to SEQ ID NO: 1 of Erk1 or Erk2, wherein the Thr at position 8 of the sequence is phosphorylated, wherein the phosphorylated Thr indicates a heart disease, preferably cardiac hypertrophy (Results 1.3, 1.5). Such an assay provides a convenient tool to detect Erk1/2 phosphorylated at Thr188 e.g. in a hospital or medical practice since no extensive laboratory facility is needed.

In a further aspect, the invention relates to the use of an antibody specific to SEQ ID NO: 1 of Erk1 or Erk2, wherein the Thr at position 8 of the sequence is phosphorylated for manufacturing an assay for detecting the presence and/or the amount of phosphorylated Erk1/2 in a sample.

In a further aspect, the invention relates to the use of an antibody specific to SEQ ID NO: 1 of Erk1 or Erk2, wherein the Thr at position 8 of the sequence is phosphorylated for manufacturing an assay for analyzing the hypertrophic stimulus of a patient (Results 1.10).

In a further aspect, the invention relates to the use of an antibody specific to SEQ ID NO: 1 of Erk1 or Erk2, wherein the Thr at position 8 of the sequence is phosphorylated for manufacturing an assay for detecting Erk1/2 signaling activity in tissue, preferably in heart or cancer tissue (Results 1.11, FIG. 8).

In a further aspect, the invention relates to the use of angiotensin II in an assay for detecting the presence and/or the amount of phosphorylated Erk1/2 in a sample. angiotensin II can be used to stimulate $G_q$-coupled AT1-receptors, thereby inducing phosphorylation of Erk1/2 at Thr188. Therefore, angiotensin II is particularly for use as a positive control in assays for detecting phosphorylated Erk1/2 (Results 1.3, FIG. 2 *a*).

In a further aspect, the invention relates to the use of neuregulin in an assay for detecting the presence and/or the amount of phosphorylated Erk1/2 in a sample. Neuregulin can be used to enhance $G\alpha_{q/11}$-activity, thereby inducing phosphorylation of Erk1/2 at Thr188. Therefore, neuregulin is particularly suitable for use as a positive control in assays for detecting phosphorylated Erk1/2 (Results 1.4, FIG. 3.1 *b-g*).

Figure 7:
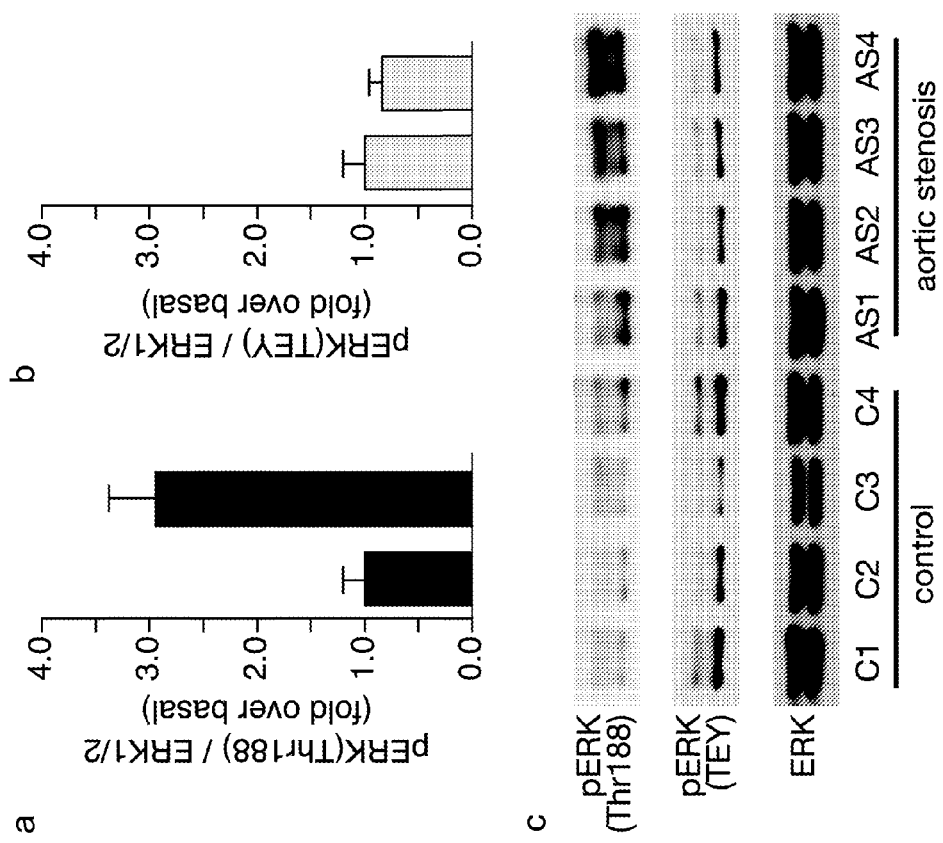
FIG. 7 shows the analysis of Thr188-phosphorylation as a marker of cardiac hypertrophy in patients.

In a further aspect, the invention relates to the use of an antibody specific to SEQ ID NO: 1 of Erk1 or Erk2, wherein the Thr at position 8 of the sequence is phosphorylated for manufacturing a pharmaceutical composition for the treatment of a disease selected from the group consisting of heart diseases, in particular heart failure, cardiac hypertrophy, interstitial fibrosis, cardiac dysfunction, aortic valve stenosis, cancer, in particular cancer of epithelial origin, colorectal adenocarcinoma, colon adenocarcinoma, lung adenocarcinoma, basal lung squamous cell carcinoma and small cell lung carcinoma (Results 1.10, 1.11, FIG. 7, FIG. 8).

In a further aspect, the invention relates to a peptide of SEQ ID NO: 4. This peptide shows almost complete homology with SEQ ID NO: 1, from which it is derived, except that the Thr at position 8 is replaced by Aspartic acid (Asp, D). This amino acid exchange mimics a Thr phosphorylation, such that an Erk2 which contains SEQ ID NO: 4 instead of SEQ ID NO: 1 (Erk2$^{T188D}$) exhibits a "gain-of-function"-phenotype (Results 1.5, FIG. 3 b).

In a further aspect, the invention relates to a peptide of SEQ ID NO: 5. This peptide shows almost complete homology with SEQ ID NO: 1, from which it is derived, except that the Thr at position 8 is replaced by serine (Ser, S). This amino acid exchange prevents the phosphorylation of the peptide at the amino acid at position 8, such that Erk2 which contains SEQ ID NO: 5 instead of SEQ ID NO: 1 (Erk2$^{T188S}$) represents a phosphorylation deficient mutant (Results 1.5, FIG. 3 a, FIGS. 3.1 f, g).

In a further aspect, the invention relates to a peptide of SEQ ID NO: 6. This peptide shows almost complete homology with SEQ ID NO: 1, from which it is derived, except that the Thr at position 8 is replaced by alanine (Ala, A). This amino acid exchange prevents the phosphorylation of the peptide at the amino acid at position 8, such that Erk2 which contains SEQ ID NO: 6 instead of SEQ ID NO: 1 (Erk2$^{T188A}$) represents a phosphorylation deficient mutant (Results 1.5, FIG. 3 c-e, FIGS. 3.1 f, g).

In a further aspect, the invention relates to the use of the peptide of SEQ ID NO: 4 and/or of Erk2$^{T188D}$ for potentiating growth-factor induced gene expression and cell cycle entry triggered by Erk1/2 in vitro.

In a further aspect, the invention relates to the use of the peptide of SEQ ID NO: 4 and/or of Erk2$^{T188D}$ for potentiating hypertrophic phenotypes of cells in vitro (Results 1.5, 1.8, FIG. 3 a, FIGS. 3.1 f, g, FIG. 5 e).

In a further aspect, the invention relates to the use of the peptide of SEQ ID NO: 5 and/or SEQ ID NO: 6 and/or of Erk2$^{T188S}$ and/or Erk2$^{T188A}$ for attenuating and/or inhibiting hypertrophic phenotypes in cells in vitro (Results 1.5, 1.8, FIG. 3 l, FIGS. 5 d, e).

In a further aspect, the invention relates to the use of SEQ ID NO: 1 in which the Thr at position 8 of the sequence is phosphorylated for triggering hypertrophic phenotypes in cells in vitro (Results 1.8).

In a further aspect, the invention relates to the use of SEQ ID NO: 1 for producing an antibody specific to SEQ ID NO: 1 of Erk1 or Erk2, wherein the Thr at position 8 of the sequence is phosphorylated (Example 2.3)

In a further aspect, the invention relates to the use Erk$^{\Delta 174-177}$ for manufacturing a pharmaceutical composition for the treatment of a disease selected from the group consisting of heart diseases, in particular heart failure, cardiac hypertrophy, interstitial fibrosis, cardiac dysfunction, aortic valve stenosis, cancer, in particular cancer of epithelial origin, colorectal adenocarcinoma, colon adenocarcinoma, lung adenocarcinoma, basal lung squamous cell carcinoma and small cell lung carcinoma (Results 1.8, 1.10, 1.11, FIG. 5 a-c, FIG. 7, FIG. 8). The pharmaceutical composition is suitable for inhibiting the interaction and thus the activation of Erk1/2 by sequestering the endogenous Erk1/2 molecules.

In a further aspect, the invention relates to a method for treating a patient suffering from heart failure comprising administering a pharmaceutically effective amount of antibody specific to SEQ ID NO: 1 of Erk1 or Erk2, wherein the Thr at position 8 of the sequence is phosphorylated, to the patient.

In a further aspect, the invention relates to a method for treating a patient suffering from heart failure comprising administering a pharmaceutically effective amount of a peptide comprising SEQ ID NO: 5 to the patient.

In a further aspect, the invention relates to a method for treating a patient suffering from heart failure comprising administering a pharmaceutically effective amount of a peptide comprising SEQ ID NO: 6 to the patient.

EXPERIMENTAL RESULTS AND EXAMPLES

1. Experimental Results 1.1 A New Autophosphorylation Site at Threonine 188 of ERK1/2

The observation that Raf1 binds to G-protein βγ-subunits (G βγ) (Slupsky, 1999) led us to investigate the potential of G-proteins, some of which can also trigger cardiac hypertrophy, to interact with proteins of the Raf/MEK/ERK1/2-cascade and to affect their activity and cellular localization.

1.2 G βγ Induce Autophosphorylation of Erk2 at Thr188

Purified active His$_6$-tagged Mek1$^{SS218/222DD}$ (simulating the Raf1-phosphorylated, active state[3]; termed Mek*) or His$_6$-Erk2 (which is always partially active when purified) co-precipitated purified G βγ suggesting direct interactions (FIG. 1a). Co-incubation of purified Erk2 with purified G βγ caused increased phosphorylation of Erk2 to an extent similar to that caused by Mek* (FIG. 1b). However, this phosphorylation did not appear to occur in the TEY-motif (as revealed by specific antibodies, FIG. 1b) nor did it increase Erk2-activity (FIG. 1.1a). Since the Gβγ-preparation contained no kinase activity towards Erk2 (FIG. 1.1b), these results show G βγ-induced autophosphorylation of Erk2 at a site distinct from the TEY-motif.

To identify this site, the inventors analyzed the phosphorylation pattern of Erk2 by two-dimensional phosphopeptide mapping followed by phospho-amino acid analyses (FIGS. 1c, d). Incubation of purified Erk2 alone with [γ-$^{32}$P]ATP resulted in a single phosphopeptide, P1, containing only phosphotyrosine, identified as the Tyr185-autophosphorylated peptide by mutating Tyr185 to Phe185. Incubation with Mek* yielded one additional phosphopeptide, P2, containing phosphotyrosine and -threonine, representing the phosphorylation at Thr183/Tyr185.

A third phosphopeptide, P3, containing only phosphothreonine was observed after incubation of Erk2 with Gβγ (FIGS. 1c,d). Incubation of Erk2 with both Gβγ and Mek* generated all three phosphopeptides, indicating that P3 is distinct from P1 and P2 (FIG. 1.1c). Mutation of Tyr185 to Phe185, which prevents autophosphorylation and—activation of Erk2, abolished the appearance of phosphopeptide P3 after co-incubation with G βγ, indicating that P3 was dependent on active Erk2 and, thus, generated by autophosphorylation of Erk2.

This autophosphorylation was shown to occur on Thr188: First, all threonine-residues of Erk2 were mutated to alanine and analyzed by phosphopeptide mapping. Only the Erk2$^{T188A}$-mutant showed a loss of G βγ-induced phosphopeptide P3, while Mek*-induced phosphorylation and autophosphorylation remained unaffected (FIG. 1e and data not shown in the figure). An Erk2$^{T188S}$-mutant with a more similar amino acid exchange also showed almost no P3 (FIG. 1.1d). Second, phosphoErk(Thr188)-specific antibodies were generated, which gave a signal only after incubation of Erk2 with Gβγ, but not with Mek* (FIG. 1f); these antibodies revealed no signal for Erk2$^{T188A}$ nor when pre-incubated with phosphoErk(Thr188)-peptide (FIGS. 1.1e,f). The inventors termed this phosphorylation, which occurs in corresponding regions of Erk1/2-isoforms in other species (FIG. 1.1g), Thr188-phosphorylation.

1.3 Thr188-Phosphorylation in Hypertrophy and Heart Failure

In order to examine whether Gβγ-induced Thr188-phosphorylation plays a role in cardiac hypertrophy, the inventors analyzed mouse hearts three weeks after inducing pressure-overload by transverse aortic constriction (TAC). TAC induced a stable interaction of Raf1 and of Erk1/2 with Gβγ in the hearts as shown by co-immunoprecipitation as well as strong Thr188-phosphorylation of Erk1/2 (FIGS. 1g,h). A≈5-fold increase in Thr188-phosphorylation was also observed in failing human hearts, comparable in extent to classical ERK1/2-phosphorylation at Thr183/Tyr185 (FIG. 1i). These data indicate that Gβγ-dependent Thr188-phosphorylation of ERK1/2 plays a role in cardiac hypertrophy and failure.

To investigate the specificity of upstream stimuli that initiate G βγ-dependent Thr188-phosphorylation, the inventors treated neonatal rat cardiomyocytes (NRCM) either with angiotensinII, which triggers hypertrophy via $G_q$-coupled $AT_1$-receptors, or with carbachol, a non-hypertrophic stimulus activating cardiac $G_i$-coupled $M_2$-muscarinic receptors (Sugden and Clerk, 1998, Brown et al., 1997). Stimulation with angiotensinII, but not with carbachol, markedly enhanced co-immunoprecipitation of Gβγ with both Raf1 and Erk1/2 (FIG. 2a). Investigation of further stimuli in transfected cell lines revealed that $G_q$-coupled receptors ($M_1$-muscarinic, $α_1$-adrenergic) caused direct interaction of Erk1/2 with Gβγ, while $G_i$-coupled receptors ($M_2$-muscarinic, $α_{2A}$-adrenergic) did not. Similarly, stimulation of the hypertrophic $AT_1$- and $α_1$-adrenergic, but not of the non-hypertrophic $M_2$-muscarinic receptors in cardiomyocytes (Sugden and Clerk, 1998, Brown et al., 1997), induced Thr188-phosphorylation of Erk1/2, while all three caused classical Erk1/2-phosphorylation in the TEY-motif. This was true for short-term stimulation in adult cardiomyocytes and for long-term, hypertrophic stimulation in neonatal cardiomyocytes (FIGS. 2c,d, FIGS. 3.1a,b).

1.4 Receptor Tyrosine Kinases (RTK) Induce Thr188 Phosphorylation

Interestingly, neuregulin1-β1, a hypertrophic agonist that activates the receptor tyrosine kinase ErbB, also induced Thr188-phosphorylation of Erk1/2 in cardiomyocytes (FIGS. 2c,d). Experiments showed that it also involved Gβγ (FIG. 3.1b-g). First, transfection of the GRK2-C-terminus, a Gβγ-scavenger (Lorenz et al., 2003), inhibited not only angiotensinII—but also neuregulin-mediated protein synthesis and cytoskeletal rearrangement in neonatal cardiomyocytes. Second, neuregulin-stimulation of neonatal cardiomyocytes permitted co-immunoprecipitation of Gβγ with Raf1 or Erk1/2. Third, neuregulin-stimulation of cardiomyocytes triggered phosphorylation of $Gα_{q/11}$ at Tyr356, which enhances $Gα_{q/11}$-activity, and mutation of this Tyr356 to phenylalanine blocked neuregulin-induced hypertrophic protein synthesis. Fourth, also neuregulin-induced protein synthesis was impaired by Erk$^{T188A}$- and Erk$^{T188S}$-mutants. Since an inhibitor (PP2) of Src-kinase blocked these effects, the interaction between ErbB and Thr188-phosphorylation is presumably indirect. In summary, the data suggest that Thr188-phosphorylation can mediate cross-talk between receptor tyrosine kinases and G-proteins.

1.5 Thr188-Phosphorylation is Causally Related to Hypertrophy

Thr188-phosphorylation of Erk1/2 occurred in response to TAC or various hypertrophic stimuli. Several lines of experimentation suggest that Thr188-phosphorylation plays a causal role in cardiac hypertrophy. First, in neonatal cardiomyocytes overexpression of the phosphorylation-deficient Erk2$^{T188S}$-mutant effectively inhibited angiotensinII—as well as neuregulin-induced protein synthesis (FIG. 3a, FIGS. 3.1f,g). Second, Erk2$^{T188D}$, which mimics Thr188-phosphorylation, exhibited a "gain-of-function"-phenotype in neonatal cardiomyocytes: it conferred to the non-hypertrophic $M_2$-receptor stimulus carbachol the surprising ability to increase protein synthesis, to induce cardiomyocyte growth (FIG. 3b). These results show that Thr188-phosphorylation is causally involved in activating the pro-hypertrophic functions of Erk1/2 in cardiomyocytes.

To assure the specificity of these Erk2$^{T188}$-mutants the inventors verified that they were not altered in their kinase abilities, sensitivity to upstream stimulation or in their Gβγ-binding properties. When the various HA-tagged Erk2$^{T188}$-mutants were precipitated from transfected HEK293-cells, co-precipitated Gβγ and kinase activity (MBP-phosphorylation assays) were indistinguishable from wild-type Erk2 and increased to similar extents after stimulation of endogenous $M_3$-receptors. In addition, the Gβγ-dependent inositol phosphate production (an assay of Gβγ-function) was equally suppressed by all Erk2$^{T188}$-mutants. These controls showed that with the exception of Thr188-phosphorylation these mutants behaved normally.

The significance of Thr188-phosphorylation of Erk1/2 for the development of cardiac hypertrophy in vivo was then tested in several transgenic mouse lines with cardiac-specific expression: Erk2$^{T188A}$ and Erk2$^{T188S}$ (phosphorylation-deficient), Erk2$^{T188D}$ ("gain-of-function") and wt-Erk2 as a control (=Erk2$^{T188T}$; in addition to wild-type, background FVB/N-mice). Again, TAC was used to induce hypertrophy, and mice were then analyzed for gross cardiac morphology, histology and by echocardiography and cardiac catheterization (FIG. 3c-h). No abnormalities were detected without TAC. TAC led to an increase in morphological and echocardiographic wall thickness and heart weight (FIGS. 3c,d), which was significantly more pronounced in Erk2$^{T188D}$-, and less pronounced in the Erk2$^{T188A}$- and Erk2$^{T188S}$-lines than in control-lines (wild-type, Erk2$^{T188T}$). Very similar changes were seen in cardiomyocyte size (FIG. 3d). In addition, the extent of hypertrophy correlated with induction of the marker genes ANF and BNP (FIG. 3i-k) and interstitial fibrosis (FIG. 3e).

Fractional shortening and left ventricular contractility (dp/$dt_{max}$) and relaxation (dp/$dt_{min}$) were reduced by TAC only in Erk2$^{T188D}$-mice, indicating cardiac dysfunction (FIG. 3f-h). These effects became more prominent when mouse hearts were stimulated with dobutamine. Intriguingly, cardiac function was not depressed in Erk2$^{T188A}$- and Erk2$^{T188S}$-mice. In addition, Erk2$^{T188S}$ attenuated the hypertrophic response to application of angiotensinII for 14 days (FIG. 3l).

Furthermore, as in cardiomyocytes (FIG. 3b), the Erk2$^{T188D}$-mutation converted carbachol/$M_2$-receptor stimulation for 14 days into a hypertrophic stimulus (FIG. 3l). While carbachol induced no hypertrophy in control mice (wild-type or Erk2$^{T188T}$), it increased heart weight, wall thickness and ANF- and BNP-expression in Erk2$^{T188D}$-mice (FIGS. 3m,n).

Interestingly, under basal and under TAC-conditions, Erk1/2-phosphorylation at the TEY-motif, Erk1/2-activities towards MBP and also co-immunoprecipitated Gβγ (overexpressing or not) were similar in all hearts. Only when Erk1/2 in the lysates was maximally phosphorylated with purified Mek* prior to the MBP-activity assays, did the different Erk2-transgenic mice exhibit higher Erk-activities, correlating with the degree of Erk2-overexpression. This suggests that total Erk1/2-activity in the heart might be limited by upstream signals rather than by the Erk1/2-expression level. It further indicates that the phenotype of Erk$^{T188D}$-mice is not due to altered kinase activity or Gβγ-binding.

Taken together, the data in transgenic mice indicate that Thr188-phosphorylation plays a key role in Erk1/2-mediated cardiac hypertrophy. Its blockade inhibited cardiac hypertrophy, and its simulation enhanced TAC-induced hypertrophy or caused hypertrophy together with a normally non-hypertrophic $M_2$-receptor stimulus.

1.6 Activation of the Entire MAPK-Cascade is Necessary for Gβγ/Erk1/2-Interaction Since upstream activation of the MAPK-cascade by a (hypertrophic) stimulus was essential for Gβγ-interactions with Raf1 or Erk1/2, for Thr188-phosphorylation and for the Erk2$^{T188D}$-mouse phenotype, the inventors further analyzed the role of the upstream kinases for Gβγ/Erk1/2-interactions.

Immunoprecipitation of HA-tagged Raf1 from HEK293-cells co-precipitated not only Gβγ but also Erk1/2 after stimulation of $G_q$-coupled $M_3$-receptors (FIG. 4a). Further experiments revealed that Gβγ-binding to the MAPK-cascade proteins depends on the formation of a complex that includes all members of the MAPK-cascade. Silencing endogenous Raf1 expression by RNA-interference or inhibition of MEK1/2 markedly reduced co-immunoprecipitation of Gβγ with Erk1/2 (FIGS. 4b,c). In line with this observation, inhibition of the MAPK-cascade by silencing Raf1, applying PD98059, or overexpressing the dominant-negative Mek1$^{K97M}$ or Erk-2$^{T183A,Y185A}$ all prevented Gβγ-scavenging as reflected by increased Gβγ-dependent inositol phosphate formation after carbachol-stimulation (FIG. 4d-f). These results suggest that Gβγ act as a scaffold for the entire MAPK-cascade.

1.7 Dimerization is Needed for Gβγ-Binding and Thr188-Phosphorylation

To further delineate the mechanisms of Gβγ-binding and Thr188-phosphorylation, the inventors analyzed the Gβγ/Erk2-interface by investigating Erk2 truncation mutants for Gβγ-binding in co-immunoprecitation studies and Gβγ-dependent inositol phosphate formation. These experiments showed that the kinase domain (AA22-318) is essential for Gβγ-interactions (FIGS. 4g,h). The kinase domain is also important for homo-dimerization of Erk1/2 (Khokhlatchev et al., 1996). To test if Erk1/2-dimerization might play a role in Gβγ-binding and Thr188-phosphorylation, dimer-formation was investigated using HA-tagged wild-type Erk2 and Flag-tagged Erk2-constructs (wt-ERK2, Erk2$^{\Delta174-177}$, Erk2$^{T188S}$ and Erk2$^{T188D}$). Co-precipitation assays showed that stimulation of $G_q$-coupled $M_1$- (FIG. 4i) and $G_i$-coupled $M_2$-muscarinic receptors induced dimers of Erk2 with the Erk2$^{T188}$-mutants, but not with the known dimerization-deficient Erk2$^{\Delta174-177}$-mutant.

Incubation of Erk2 with Gβγ yielded exclusively phosphopeptides with either Thr188- or Tyr185-phosphorylation. This is compatible with intermolecular phosphorylation of an inactive Erk2-molecule by a Tyr185-phosphorylated Erk2-molecule in an Erk2-dimer. Indeed, incubation of Erk2$^{\Delta174-177}$ with Mek* produced phosphopeptides P1 and P2, but Gβγ failed to produce P3, indicating a lack of Thr188-phosphorylation (FIG. 4j). These findings show that dimerization of Erk2 is necessary for Gβγ-binding and for Thr188-phosphorylation.

1.8 Thr188-Phosphorylation Promotes Nuclear Localization of Erk1/2

To investigate downstream effects of Thr188-phosphorylation that might cause cardiac hypertrophy, the inventors determined phosphorylation of Erk1/2-targets in the Erk$^{T188}$-mouse lines (FIGS. 5a,b). Elk1, MSK1, c-Myc and p90RSK are relevant Erk1/2-targets in cardiac myocytes (Sugden and Clerk, 1998). Their basal phosphorylation was similar for all Erk$^{T188}$-mouse lines. TAC increased phosphorylation of the cytosolic proteins p90RSK and p70S6K[1], but similarly in all lines (FIG. 5b), suggesting that Thr188-phosphorylation did not affect the phosphorylation of cytosolic Erk1/2-substrates.

In contrast, for nuclear targets (Elk1, MSK1, c-Myc) there were pronounced differences (FIG. 5a): TAC modestly increased their phosphorylation in control hearts (wild-type, Erk2$^{T188T}$), but massively in Erk2$^{T188D}$-hearts and almost not in Erk2$^{T188S}$- and Erk2$^{T188A}$-hearts. These data parallel the hypertrophic effects of Erk$^{T188}$-mutants (FIG. 3) and suggest that Thr188-phosphorylation specifically increases phosphorylation of nuclear Erk1/2-targets.

Confocal microscopy of the sub cellular distribution of YFP-tagged Erk2$^{T188}$-mutants strengthened this hypothesis (FIG. 5c). Basal nuclear-to-cytosolic ratios were similar in all Erk-mutants. However, stimulation of co-transfected $G_q$-coupled $M_1$-receptors induced nuclear localization of wild-type Erk2 and Erk2$^{T188D}$, while the nuclear-to-cytosolic distribution of Erk2$^{T188S}$ was unaffected. In contrast, after stimulation of $G_i$-coupled receptors only Erk2$^{T188D}$ localized to the nucleus, while both wild-type and Erk2$^{T188S}$ remained unaffected.

Likewise, immunohistochemistry in sections of Erk2$^{T188}$-hearts showed that TAC caused pronounced nuclear Erk2$^{T188D}$-localization, while this was modest in wild-type and almost absent in Erk2$^{T188A}$-hearts (FIG. 5d). In parallel, nuclear Elk1-phosphorylation after TAC was marked in sections of Erk2$^{T188D}$-hearts, modest in wild-type and weak in Erk2$^{T188S}$-hearts (FIG. 5e). And finally, immunohistochemical detection of phosphorylated Erk1/2-forms showed essentially nuclear localization of Thr188-phosphorylated Erk1/2, whereas TEY-phosphorylated Erk1/2 was both cytosolic and nuclear (FIG. 5e).

Taken together, these data show that Thr188-phosphorylation (in the presence of the canonical stimulus) triggers nuclear localization of Erk1/2 and phosphorylation of nuclear targets such as Elk1 that are known to initiate cardiac hypertrophy.

1.9 Thr188-Phosphorylation of Erk1/2 is a Sustained Process

If Thr188-phosphorylation is important for cardiac hypertrophy, it should be a long-term process. Indeed, the time-course of Thr188-phosphorylation was considerably slower and more sustained than that of phosphorylation at the TEY-motif in HEK293-cells with $M_3$-receptor stimulation over 60 min (FIG. 6a) as well as in mouse hearts after TAC over up to four months (FIG. 6b) or during 14 days of angiotensinII-treatment (data are not shown in the figure). In all three models, TEY-phosphorylation reached a maximum and then declined or oscillated. In contrast, Thr188-phosphorylation showed steady, continuous increases over long time-spans—consistent with a role in the long-term process of cardiac hypertrophy.

1.10 Thr188-Phosphorylation of Erk1/2 as a Marker of Cardiac Hypertrophy

In a clinical pilot study on patients with aortic valve stenosis, the correlation between ERK-phosphorylation at Thr188 and the degree of left ventricular hypertrophy was studied, with the aim of evaluating whether Thr188-phosphorylation can serve as a quantitative indicator of the hypertrophic stimulus and a possible predictor of the clinical outcome. In the clinical pilot study the Thr188-phosphorylation was assessed as a marker of hypertrophy in a small cohort of patients. Patients with aortic valve stenosis often develop cardiac hypertrophy due to increased left ventricular wall stress. The inventors have collected and analyzed four such patients, which underwent the general CHFC data set characterization. The degree of hypertrophy was assessed by pre-operative ultrasound.

TABLE 1

IVSd, diastolic interventricular septum; AS, aortic stenosis. The post-operative course of these patients was uneventful; the long-term course of these patients willbe evaluated as described in the study proposal.

| patient sample | IVSd |
|---|---|
| AS1 | 1.2 cm |
| AS2 | 1.4 cm |
| AS3 | 1.3 cm |
| AS4 | 1.2 cm |

Hypertrophied septum was removed during valve surgery replacement by left ventricular outflow tract myocardial resections and the hypertrophied myocardium was tested for the intensity of ERK1/2-phosphorylation at Thr188. These samples were compared to healthy control ventricular tissue from four organ donors, whose hearts were not transplanted for technical reasons. The data show that Thr188-phosphorylation of ERK1/2 was tripled in patients with septal hypertrophy accompanying aortic valve stenosis (FIG. 7). Further, these data show that this phosphorylation is stable enough to serve as a potential marker of cardiac hypertrophy. This was in pronounced contrast to the canonical phosphorylation of ERK1/2 (at Thr183 and Tyr183), which was not elevated in patients with aortic stenosis. This may be due to a fast dephosphorylation process of these phosphorylation sites.

1.11 Thr188-Phosphorylation is Highly Expressed in Epithelial Derived Cancer

Surprisingly, the inventors found, that Erk1/2 phosphorylated at Thr188 not only occurs in failing hearts but is also prevalent in cancer tissue. Tissues derived from different types of cancer were analyzed and it was discovered that, in contrast to canonical phosphorylation at Thr183 and Tyr185, the phosphorylation of Erk1/2 at Thr188 was markedly increased in cancer types of epithelial origin, e.g. colorectal adenocarcinoma, colon adenocarcinoma, lung adenocarcinoma, basal lung squamous cell carcinoma, lung adenocarcinoma and small cell lung carcinoma. (FIG. 8). In some cancers canonical phosphorylation was even reduced compared to healthy tissue.

1.12 Inventor's Comments on Results

Taken together, the MAPK-cascade integrates various signaling components to elicit multiple biological responses (Bogoyevitch and Sudgen, 1996, Bogoyevitch and Sudgen, 1996, Brunet et al., 1999). Canonical activation of ERK1/2 requires dual phosphorylation at the TEY-motif by MEK1/2.

A new cascade was shown to be involved in protein-protein interactions between ERK1/2 and Gβγ that results in such a modification of ERK1/2, Thr188-phosphorylation, which then directs ERK1/2 towards nuclear targets. This mechanism (FIG. 6c) depends on (a) the activation of the entire Raf/MEK/ERK cascade and subsequent phosphorylation of ERK1/2 within the TEY-motif, (b) dimerization of ERK, and (c) upstream signals contributing Gβγ, specifically activation of $G_q$-coupled receptors. The integration of these three signaling components leads to autophosphorylation of ERK2 at Thr188 (Thr208 in ERK1). This autophosphorylation is of a sustained nature suggesting that it is quite resistant to dephosphorylation.

It was demonstrated that Thr188-phosphorylation is causally and specifically involved in the induction of cardiac hypertrophy in vitro and in vivo, because it directs ERK1/2 to the nucleus and to the phosphorylation of substrates such as Elk1, MSK1 and c-Myc. These proteins have all been shown to be involved in cardiomyocyte hypertrophy (Sugden and Clerk, 1998, Bogoyevitch and Sudgen, 1996) Interestingly, Thr188-phosphorylation does so without affecting the overall kinase activity of ERK1/2. Thus, ERK1/2 integrates upstream signals and encodes them in different phosphorylations (Thr183/Tyr185 for activation; Thr188 for nuclear targeting) to cause cardiac hypertrophy. Spatio-temporal regulation of the ERK1/2 is a crucial determinant to trigger specific biological responses to extracellular signals, and translocation of activated ERK1/2 to the nucleus is essential for growth factor-induced gene expression and cell cycle entry. The data show for the first time that the integration of classical activation with $G_q$-mediated activation can lead to accumulation in the nucleus caused by increases of either nuclear translocation or nuclear retention.

Interestingly, also neuregulin and the mechanical stress caused by TAC can apparently recruit Gβγ to the MAP-kinase cascade and thereby initiate Thr188-phosphorylation, suggesting a new important link between different signaling cascades. Moreover, since signaling via RTKs is an important feature in cancer development and the inventors could show that Thr188 phosphorylation of ERK1/2 is mediated via this phosphorylation, the inventors concluded, that it is not only a molecular switch for cell hypertrophy but also for proliferation of cancer cells.

Thr188-phosphorylation initiates hypertrophy in cardiomyocytes and is found in hypertrophied mouse hearts and in failing human hearts. Transgenic mice expressing $ERK^{T188D}$, which mimics constitutive Thr188-phosphorylation, develop excessive cardiac hypertrophy after TAC and even after the non-hypertrophic stimulus carbachol, while mice expressing ERK2 lacking this phosphorylation site showed an attenuated hypertrophic response. This newly discovered Thr-188 phosphorylation of ERK1/2 appears to permit distinction of downstream targets that mediate the distinct biological effects of different types of ERK1/2 activation. It is also important to analyze whether Thr188-phosphorylation also occurs in other proliferative responses that involve ERK1/2. Our data show that this mechanism is critical for maladaptive cardiac hypertrophy, but it may be fundamental to many other hypertrophic and proliferative diseases.

2. Examples 2.1 MBP-Phosphorylation Assay In Vitro

The inventors determined the kinase activity by incubating purified $His_6$-Erk2 in 20 mM HEPES, pH 7.2, 2 mM EDTA, 100 µM ATP and 10 mM $MgCl_2$ with 1 µM kinase in the presence or absence of purified Gβγ (500 nM) (Lorenz et at, 2003) or $His_6$-Mek1$^{SS218/222DD, \Delta 32-51}$ (2.5 nM). After 5 min of preincubation, the inventors added [γ-$^{32}$P]ATP (and 7.5 µg MBP per 50 µl) and let the reaction proceed for another 5 min at 30° C.

2.2 Two-Dimensional Phosphopeptide Mapping of Recombinant Erk2

The inventors incubated purified $His_6$-Erk2, $His_6$-Erk2$^{T188A}$, $His_6$-Erk2$^{T188S}$, $His_6$-Erk2$^{\Delta174\text{-}177}$ or $His_6$-Erk2$^{Y185F}$ (1 μM) with Gβγ-subunits (500 nM)[30] in the presence or absence of $His_6$-Mek1$^{SS218/222DD,\Delta32\text{-}51}$ (5 nM) in 20 mM HEPES, pH 7.2, 2 mM EDTA, 10 μM ATP, 10 mM $MgCl_2$ and 100 μM [γ-$^{32}$P]ATP for 20 min at 30° C. The inventors separated proteins by SDS-PAGE, transferred them to a PVDF membrane and visualized them with Ponceau S. The inventors then digested $His_6$-Erk2, $His_6$-Erk2$^{T188A}$, $His_6$-Erk2$^{T188S}$ $His_s$-Erk2$^{\Delta174\text{-}177}$ or $His_6$-Erk2$^{Y185F}$ with trypsin before separating the phosphopeptides by two-dimensional phosphopeptide mapping via electrophoresis (first dimension) and thin layer chromatography (second dimension) as described (Lorenz et al., 2003).

2.3 Antibodies used for immunodetections of proteins.

The inventors used the following antibodies for immunoprecipitation (IP), immunoblotting (IB) or immunohistochemistry (IHC): antibodies to Flag (F3165, Sigma; IP, IB), HA (clone 12CA5, Roche; IP), HA (Hiss Diagnostics; IB), phosphoMSK1 (Thr581) (9595, Cell Signaling; IB), MSK1 (sc-25417, Santa Cruz; IB), phospho-cMyc (Thr58/Ser62) (9401, Cell Signaling; IB), cMyc (9402, Cell Signaling; IB), phospho-p90RSK (Ser380) (9341, Cell Signaling; IB), RSK1/RSK2/RSK3 (9347, Cell Signaling; IB), phosphoElk1 (Ser383) (9186, Cell Signaling (IB); 90121-1, Imgenex (IHC)), Elk1 (9182, Cell Signaling; IB), p70S6 kinase (Thr421/Ser424) (9204, Cell Signaling; IB), p70S6 kinase (9202, Cell Signaling, IB), Gβ (sc-378, Santa Cruz; IP, IB), pTyr (sc-18182, Santa Cruz; IB) or Gα$_{q/11}$ (sc-26791, Santa Cruz; IP, IB), Raf1 (R19120, BD Biosciences; IP, IB), MEK1 (sc-18, Santa Cruz; IP, IB), ERK1/2 (9102, Cell Signaling; IP, IB), phosphoERK1/2 (9101, Cell Signaling; IB, IHC), Erk2 antibodies raised against recombinant $His_6$-Erk2 (Biogenes; IB, IHC) and phosphoERK(Thr188) antibodies. The inventors raised phosphoERK(Thr188)-specific antibodies against a synthetic peptide corresponding to residues 181-195 of mouse Erk2. To do so the peptide of SEQ ID NO: 1 was repeatedly injected into a rabbit at intervals of several weeks to stimulate immunization, in particular specific B cells to produce large amounts of the antibody in the blood. To improve immunization the peptide can be conjugated to a carrier protein, e.g. bovine serum albumin or keyhole limpet hemocyanin, or it can be administered together with an adjuvant. The antiserum was harvested from the rabbit using commonly used methods known to the person skilled in the art. After cleaning the antisera from peptide-specific antibodies using a CNBr-sepharose column containing unphosphorylated peptide, the inventors isolated the phosphospecific antibodies via a column containing the immunogenic, phosphorylated peptide (FLTEYVA-(p)T-RWYRAPE-amide conjugated to *Limulus polyphemus* hemocyanine (Biogenes). The inventors always supplemented the anti-phosphoERK (Thr188) antibody solutions with the unphosphorylated peptide (≈7.5 μg ml$^{-1}$). The inventors prepared cell lysates and heart lysates from transgenic Erk2 mice as described below.

2.4 Immunoblot detection of phosphoThr188 in vitro.

For detection of phosphoErk(Thr188) in vitro, the inventors incubated $His_6$-Erk2 or $His_6$-Erk2$^{T188A}$ without or with ATP (10 μM) and Gβγ (60 nM) in the presence or absence of $His_6$-Mek1$^{SS218/222DD,\Delta32\text{-}51}$ (Mek1*, 10 nM) in 20 mM HEPES, pH 7.2, 2 mM EDTA and 10 mM $MgCl_2$ for 20 min at 30° C. The inventors separated proteins by urea SDS-PAGE, followed by immunoblot analysis.

2.5 Human Heart Samples

In accordance with the Declaration of Helsinki, written informed consent had been obtained from all participants or the family of prospective heart donors before cardiectomy. The Ethical Committee of the Würzburg Medical Faculty, Germany, approved the experiments. The inventors obtained samples of human failing hearts from individuals undergoing heart transplantation due to end-stage heart failure (NYHA IV). Samples from ten non-failing donor hearts that could not be transplanted for technical reasons served as controls. Donor histories and echocardiography showed no signs of pathological heart function. After cardiectomy, left ventricular samples were frozen in liquid nitrogen and stored at −80° C.

2.6. Transgenic Mice

Care of the animals was taken in accordance with the institutional guidelines, and the Committee on Animal Research of the regional government (Regierung von Unterfranken, Germany) reviewed and approved all experimental protocols (reference number Az 54-2531.01-62/06). The inventors generated Erk2 and Erk2$^{T188}$-mutant transgenic mice by pronucleus injection of fertilized oocytes derived from FVB/N mice. Transgenic constructs contained the coding sequence of mouse wild-type Erk2 (T188T) or mouse Erk2 with mutations of Thr188 to alanine (T188A), serine (T188S) or aspartic acid (T188D) under the control of the mouse α-myosin heavy chain (α-Mhc) promoter.

2.7 Osmotic Minipumps

The inventors implanted osmotic minipumps (Alzet) subcutaneously in wild-type (WT; FVB/N background) mice and transgenic ERK2$^{T188}$ mutant mice (T188S, T188D, T188T) for a period of 14 days or as indicated. The pumps were either filled with angiotensinII (200 ng g$^{-1}$ h$^{-1}$) or carbachol (1 μg g$^{-1}$d$^{-1}$). The inventors used ketamine (150 μg g$^{-1}$) plus xylazine (0.5 μg g$^{-1}$) for anesthesia during surgical implantation of the minipumps. For assessment of the angiotensinII- or carbachol-induced development of cardiac hypertrophy, the inventors performed echocardiography before and 14 days after implantation and measured heart weights and tibia lengths 14 days after implantation compared to that of age-matched control animals.

2.8 Echocardiography

The inventors anesthetized mice intraperitoneally with pentobarbital (35 mg g$^{-1}$) and placed them on a heated platform (42° C.) to maintain body temperature. The inventors obtained transthoracic echocardiograms with a Vevo 770 high-resolution imaging system (VisualSonics Inc., Toronto, Canada) equipped with a 30 MHz probe (RMV-707B). The inventors obtained two-dimensional M-mode images in the short axis view at the proximal level of the papillary muscles to determine the end-diastolic and end-systolic internal diameter (LVID and LVID) and end-diastolic septal and posterior wall thickness (IVS and LVPW, respectively). Fractional shortening (FS) was calculated as follows by VisualSonics Cardiac Measurements software: FS (%)=[(LVID$_{ED}$−LVID$_{ES}$)LVID$_{ED}$$^{-1}$]×100. The inventors measured peak blood flow velocities at the site of TAC (V$_{max}$ [mm s$^{-1}$]) by Doppler ultrasound and aortic pressure gradients (PG) (mmHg) were calculated by PG=4×(V$_{max}$ 1,000$^{-1}$)$^2$.

2.9 Immunohistochemistry

The inventors dewaxed and rehydrated two-micrometer sections, incubated them in methanol containing 0.3% $H_2O_2$ for 60 min and subsequently microwaved them in 10 mM citric acid (pH 6.0) for 20 min at 700 W. After washing in 0.1 M phosphate buffer with 0.25% TritonX (TPBS), the inventors blocked the sections in TPBS supplemented with 5% normal goat serum (NGS) for 2 h at room temperature. The inventors then applied primary antibodies in TPBS supplemented with 5% NGS in dilutions (antibodies to Erk2, pErk (Thr188), pErk(TEY) or pElk1(Ser383)) overnight at 4° C. The inventors detected the primary antibodies using biotinylated goat anti-rabbit IgG followed by incubation with AB solution (Vector ABC Elite kit). The inventors then rinsed the tissue and stained it with DAB-glucose oxidase. The inventors performed counterstaining of the nuclei with hematoxylin. For control, the inventors omitted the primary antibodies.

2.10 Plasmids, Protein Expression and Purification

The inventors subcloned the cDNAs encoding mouse hemagglutinin-tagged (HA)-Mek1$^{K97M}$, HA-Erk2 (T188T or AA1-358), HA-Erk2$^{T188A}$ (T188A), HA-Erk2$^{T188S}$ (T188S), HA-Erk2$^{T188D}$ (T188D), HA-Erk2$^{\Delta174-177}$ (Δ174-177), HA-Erk2$^{T183A,Y185A}$ (dn-Erk2), HA-Erk2$^{AA22-318}$ (AA22-318), HA-Erk2$^{AA1-318}$ (AA1-318), HA-Erk2$^{AA22-358}$ (AA22-358), Flag-Erk2 (T188T), Flag-Erk2$^{T188S}$ (T188S), Flag-Erk2$^{T188D}$ (T188D), Flag-Erk2$^{\Delta174-177}$ (D174-177), YFP-Erk2 (T188T), YFP-Erk2$^{T188S}$ (T188S), YFP-Erk2$^{T188D}$ (T188D), Gα$_{11}^{Y356F}$, rat HA-Raf1, bovine GRK-2$^{495-689}$, and human α$_{2A}$-adrenergic receptor into cytomegalovirus promoter-based expression plasmids and used them for expression in eukaryotic cells. The inventors performed gene silencing of human Raf1 by RNA-interference, RNAi, by subcloning a pair of oligonucleotides producing a hairpin RNA and corresponding to positions 157-175 relative to the start codon of Raf1 into pSilencer 2.0-U6 siRNA expression vector. An unrelated control RNAi plasmid (scrambled) served as control. The inventors purchased plasmids encoding the human M$_1$- and M$_2$-muscarinic receptors from Missouri S&T cDNA Resource Center. For generation of recombinant baculoviruses, the inventors subcloned His$_6$-Mek1$^{SS218/222DD}$ into the pFastBac1 expression plasmid (Life Technologies). For protein expression in E. coli, the inventors subcloned His$_6$-Erk2-wt, His$_6$-Mek1$^{SS218/222DD,\Delta32-51}$ (Mek1*), His$_6$-Erk2$^{T188A}$ (T188A), His$_6$-Erk2$^{T188S}$ (T188S), His$_6$-Erk2$^{\Delta174-177}$ (Δ174-177) and His$_6$-Erk2$^{K52R}$, His$_6$-Erk2$^{Y185F}$ (Y185F) into the pET-3c expression vector (Novagen). The inventors expressed the proteins in E. coli (BL21) or in Spodopiera frugiperda (Sf9) cells and purified them as described (Lorenz et al., 2003). All constructs generated by PCR were sequenced entirely.

2.11 Phosphoamino Acid Analysis

The inventors eluted phosphopeptides obtained by two-dimensional phosphopeptide mapping from cellulose and hydrolyzed them in 6 N HCl. The inventors identified the free amino acids by two dimensional thin layer chromatography.

2.12 Lysate Preparation and Assessment of Protein-Gβγ Complex Formation by Co-Immunoprecipitation The inventors prepared cell lysates and tissue lysates using lysis buffer (0.5% (v/v) NP-40, 150 mM NaCl, 25 mM Na$_4$P$_2$O$_7$, 50 mM β-glycerol phosphate disodium salt, 2 mM EDTA, 2 mM EGTA, 25 mM Tris, pH 8.0, 10% (v/v) glycerol, 10 μg ml$^{-1}$ soybean trypsin inhibitor, 1 mM benzamidine, 1 mM PMSF, 50 mM NaF, 0.1 mM Na$_3$VO$_4$, 0.002% (w/v) NaN$_3$) similarly as described (Lorenz et al., 2003). The inventors determined the interaction of Gβγ with endogenous Raf1, ERK1/2, HA-tagged Raf1 or HA-tagged Erk2 constructs by immunoprecipitation with the respective antibodies (as indicated in the figures). After immunoprecipitation, the inventors detected co-immunoprecipitated proteins in immunoblot analyses using the respective antibodies (as indicated in the figures). Before lysis, the inventors incubated adult or neonatal cardiomyocytes with or without agonist as indicated (angiotensinII, 100 nM, 5 min or 24 h; carbachol, 300 μM, 10 min or 36 h; neuregulin1-β1, 20 ng ml$^{-1}$, 10 min or 24 h; phenylephrine, 35 μM, 5 min or 48 h). HEK293-cells were cultured in the absence or presence of carbachol (100 μM, 6 min) or UK14304 (1 μM, 10 min) before lysis. The inventors prepared ventricular tissue from mouse hearts derived from male 129SvEv (FIG. 1g,h), FVB/N wild-type (WT) or Erk2$^{T188}$-transgenic mice (1188T, T188D, T188S, T188A) (FVB/N background) without or after transverse aortic constriction (TAC, see Fig. legends for the duration of TAC) or carbachol-infusion. Control animals were strain-, age- and gender-matched. Lysates of ventricular tissue underwent sonification before immunoblot or immunoprecipitation assays.

2.13 Isolation of Cardiac Cells

The inventors isolated neonatal rat cardiomyocytes from hearts of 1-2 day-old Sprague Dawley rats and transfected them as described (Brown et al., 1997). The inventors isolated adult cardiac myocytes by retrograde perfusion of mouse hearts and enzymatic dissociation of cells.

2.14 Detection of Tyrosine Phosphorylated Gα$_{q/11}$

The inventors assessed phosphorylation of Gα$_{q/11}$ by immunoprecipitation of Gα$_{q/11}$ from lysates of neonatal cardiomyocytes without or with neuregulin1-β1 treatment (20 ng ml$^{-1}$, 10 min) using Gα$_{q/11}$-specific antibodies (sc-392 AC, Santa Cruz) followed by detection of phosphotyrosine and immunoprecipitated Gα$_{q/11}$ by immunoblot analyses. The inventors prepared the lysates as described above.

2.15 MBP-Phosphorylation Assay

The inventors precipitated ERK from cells or heart lysates as described above. After a final wash of immunoprecipitated proteins with 20 mM HEPES, pH 7.2 and 2 mM EDTA, the inventors started the phosphorylation reaction by adding 10 mM MgCl$_2$, 100 μM ATP, 50 μM [γ-$^{32}$P]ATP, and 6 μg MBP per 50 μl in 20 mM HEPES, pH 7.2 and 2 mM EDTA. If indicated, the inventors added His$_6$-Mek1$^{SS218/222DD,\Delta32-51}$ (Mek*, 5 nM) to the reaction. After 10 min at 30° C., the inventors separated phosphorylated proteins by SOS-PAGE and quantified the signals by PhosphorImager analysis.

2.16 MBP-Phosphorylation Assay After Addition of Gβ Specific Antibodies

The inventors assessed ERK1/2-activity in neonatal rat cardiomyocytes, HEK293-cells and COS1-cells in cell lysates prepared as described above. The inventors immunoprecipitated ERK1/2 using Erk1/2-specific antibodies (Cell Signaling or sc-93, Santa Cruz). The inventors added 100 nM IgG (control IgG raised to an unrelated protein or Gβ-specific) to assess the presence of Gβγ in the precipitated complex. After 20 min of incubation at 4° C. in 20 mM HEPES, pH 7.2 and 2 mM EDTA, phosphorylation was started by addition of 10 mM MgCl$_2$, 100 μM ATP, 50 μM [γ-$^{32}$P]ATP, and 6 μg MBP per 50 μl. After 10 min at 30° C., the inventors separated phosphorylated proteins by SDS-PAGE and quantified the signals by PhosphorImager analysis.

2.17 Determination of Protein Synthesis Rates

The inventors measured protein synthesis rates in isolated cardiomyocytes by [$^3$H]isoleucine incorporation. The inventors seeded transfected cardiomyocytes on 24-well plates in MEM supplemented with bromodeoxyuridine (25 mg l$^{-1}$), cobalamin (2 mg l$^{-1}$), NaHCO$_3$ (350 mg l$^{-1}$), penicillin (100 U ml$^{-1}$), streptomycin (100 μg ml$^{-1}$) and 5% (v/v) fetal calf serum. After 24 h, the inventors reduced the serum concentration to 1% for 1 day followed by fasting in serum-free medium for 24-48 h. Thereafter, the inventors labeled the cells with [$^3$H]isoleucine (1 μCi ml$^{-1}$) for 24-48 h in the absence or presence of 100 nM angiotensinII, 300 μM carbachol, 10 ng ml$^{-1}$ neuregulin1-β1 or 35 μM (R)-(−)-phenylephrine as indicated. The inventors measured radioactivity incorporated into the TCA (trichloroacetic acid)-precipitable material by scintillation counting.

2.18 Transverse Aortic Constriction

At the age of 8 weeks, the inventors subjected wild-type mice (WT; FVB/N background) and Erk2 transgenic mice (T188A, T188S, T188D and T188T) to transverse aortic constriction (TAC) to induce chronic left ventricular pressure overload. 6 weeks after TAC, the inventors performed echocardiography and measurements of left ventricular pressures before scarifying the animals and weighing the hearts. Measurements (echocardiography, left ventricular pressure and heart weight) of control animals were performed at the age of 14 weeks. The inventors either fixed the hearts in 4% paraformaldehyde for preparation of histological sections or snap froze them in liquid nitrogen for protein analyses.

2.19 Histological and Morphometric Analysis

For histology, the inventors fixed the hearts in 4% paraformaldehyde and embedded them in paraffin. The inventors stained the sections (2 μm) with hematoxylin and eosin or with Sirius-Red as described previously. For determination of myocyte cross-sectional areas, the inventors analyzed 35-40 individual cells per animal and 7-10 animals per genotype and group by computerized pixel counting. The inventors only included nucleated cardiac myocytes of transverse myocyte sections into the analysis. For quantification of fibrosis, the inventors stained left ventricular sections of 7-10 animals per group and genotype with Sirius-Red and subsequently analyzed four representative sections per animal by semiautomated image analysis.

2.20 Left Ventricular Catheterization

The inventors anesthetized mice with tribromoethanol (300 μg g$^{-1}$). The inventors then inserted a 1.4 F pressure catheter (Millar Instruments) into the right carotid artery and advanced it to the left ventricular chamber. Data analysis was carried out using Chart software (Chart 5.4, AD Instruments).

2.21 Northern Blot Analyses

The inventors extracted total left ventricular RNA from left ventricles using RNeasy® kits (Qiagen). The inventors separated 2 mg of total RNA in 1.2% agarose/formaldehyde gels, transferred it to Hybond-PVDF membrane (Amersham) overnight in 10×sodium chloride and sodium citrate solution (SSC), and immobilized it by UV crosslinking. The inventors labeled ANF and BNP cDNA probes (generated by PCR with the primers listed below) with [α-$^{32}$P]dCTP using the Rediprime labeling kit (Amersham). The inventors performed prehybridization at 42° C. for 2 h using Ultrahyb solution (Ambion) before adding the [$^{32}$P]-labeled probes and hybridization overnight at 42° C. The inventors washed the membranes at 42° C. in 0.1×SSC and 0.1% SDS and quantified the hybridization signals by phosphorImager analyses. The inventors used the following primers for probe generation: GAPDH forward primer 5'-CGAGAC-CCCGCTAACATCAAAT-3' (SEQ ID NO: 11); GAPDH reverse primer 5'-GCAGCCCCACAGCCATCAT-3' (SEQ ID NO: 12);; BNP forward primer 5'-TGGGGAGGCGAGA-CAAG-3' (SEQ ID NO: 13);; BNP reverse primer 5'-AGC-CCAAACGACTGACG-3' (SEQ ID NO: 14);; ANP forward primer 5'-ACCCTGGGCTTCTTCCTCGTCTTG-3' (SEQ ID NO: 15);; ANP reverse primer 5'-CCTTTTCCTCCTTG-GCTGTTATCT-3'(SEQ ID NO: 16);

2.22 Determination of Total Inositol Phosphates

For determination of total inositol phosphates, the inventors transfected HEK293-cells with the indicated Erk2-constructs. After labeling of the cells with myo-[2-$^3$H]-inositol (1 mCi ml$^{-1}$) in inositol-free DMEM for 24 h, the inventors incubated the cells in incubation buffer (137 mM NaCl, 5 mM KCl, 10 mM LiCl, 1 mM CaCl$_2$, 1 mM MgCl$_2$, 10 mM HEPES, pH 7.2) without or with carbachol (50 mM) for 15 min. The inventors extracted the inositol phosphates by addition of HClO$_4$ (20%) before neutralizing the extract with KOH (1 M), removing the precipitates by centrifugation and applying the supernatants to anion exchange columns (DowexAG1×8, Biorad). The inventors then eluted total inositol phosphates by HCl (1 M) and measured the incorporated radioactivity by scintillation counting.

2.23 Confocal Microscopy

For determination of the sub cellular distribution of YFP-tagged Erk2$^{T188}$, the inventors transfected COST-cells with one of the Erk2$^{T188}$-constructs, YFP-Erk2-wt (T188T), YFP-Erk2$^{T188S}$ (T188S) or YFP-Erk2$^{T188D}$ (T188D), and either M$_1$- or M$_2$-muscarinic receptors. 36 h after transfection, the inventors treated the cells with carbachol (100 μM, 10 min) and fixed them with 4% paraformaldehyde and 0.2% picric acid in phosphate buffer, pH 6.9 for 40 min at room temperature. After counterstaining of the nuclei with DAPI, the inventors mounted the cover slips with Fluoromount G (Biozol) and analyzed the cells using a Leica TCS SP5 confocal microscope. The inventors excited YFP with the 514 nm line of an argon laser and measured fluorescence between 600 and 650 nm. The inventors excited DAPI with a diode laser at 405 nm and measured fluorescence between 425 and 460 nm. The inventors then analyzed the data using ImageJ software.

2.24 Statistical Analysis

The inventors evaluated statistical significance by ANOVA and Bonferroni as post-hoc test, with P<0.05 regarded as significant. The inventors showed all data as means±s.e.m. The inventors reproduced individual experiments at least three times. All histological, echocardiographic and confocal evaluations were done in a blinded fashion.

DETAILED DESCRIPTION OF THE DRAWINGS

FIG. 1 Gβγ-induced autophosphorylation of Erk2 at Thr188. (a) Direct binding of Mek1$^{SS218/222DD}$ (Mek*) and of Erk2 to Gβγ using purified proteins. Con, control (bovine serum albumin). (b) [$^{32}$P]-autoradiography (upper panel) and immunoblot analyses using phospho-specific antibodies directed against phosphorylated TEY-motif of Erk1/2 (middle panel) of purified Erk2 after incubation with purified Gβγ or Mek*. (c) Two-dimensional phosphopeptide mapping of Erk2 alone, with Mek* or Gβγ. Phosphopeptides resulting from trypsin-digestion of Erk2 are designated P1, P2 and P3. (d) Phospho-amino acid analysis of the phosphopeptides P1, P2 and P3 observed in FIG. 1c. (e) Two-dimensional phosphopeptide mapping of Erk2$^{T188A}$ after incubation with Gβγ induced phosphorylation of one phosphopeptide only (P1), incubation with Mek* resulted in two phosphopeptides (P1 and P2). (f) Immunoblot analyses for Thr188-phosphorylated Erk after incubation in the absence or presence of ATP, Gβγ or Mek*, respectively. (g) Co-immunoprecipitation of Gβ with Raf1 and with Erk1/2 was only observed in lysates of hypertrophied hearts 3 weeks after transverse aortic constriction (TAC) but not in control heart lysates of sham-operated mice. Immunoprecipitations (IP) were performed using Raf1- or Erk1/2-specific antibodies (anti-Raf, anti-Erk). (h) Immunoblot analyses for Thr188-phosphorylated Erk1/2 in lysates of hypertrophied hearts (TAC) compared to control lysates of healthy hearts (con). (i) Phosphorylation of Thr188 and of the TEY-motif of ERK1/2 in failing human hearts. The ratio of the pERK(Thr188) and pERK(TEY) to the ERK1/2 signal was calculated for each individual. n=10; *, P<0.001 versus non-failing.

FIG. 1.1 Purified Gβγ induce autophosphorylation of purified Erk2 at Thr188. (a) Autoradiography of Erk2-phosphorylation (upper panel) and MBP (myelin basic protein)-phosphorylation by purified Erk2 (lower panel) after incubation with purified Gβγ or purified constitutively active Mek1$^{SS218/222DD,\Delta32-51}$ (Mek*). (b) Autoradiography of wild-type Erk2 (Erk2) (1 mM) and kinase-inactive Erk2$^{K52R}$ (1 mM) after incubation in the absence or presence of purified Gβγ (500 nM). (c) Two-dimensional phosphopeptide mapping of Erk2 after phosphorylation with Mek* and Gβγ (Erk2+Mek*+Gβγ). Phosphopeptides resulting from trypsin digestion of Erk2 are designated P1, P2 and P3. (d) Two-dimensional phosphopeptide mapping of Erk2$^{T188S}$ after incubation with Gβγ (T188A+Gβγ) induced phosphorylation of one phosphopeptide only (P1). Weak phosphorylation of P3 presumably results from residual phosphorylation of Ser188 instead of Thr188. (e) Immunoblot analysis (IB) of phosphorylated Erk1/2 at Thr188 (pErk(Thr188)) after incubation of Erk2 or Erk2$^{T188A}$ in the absence or presence of Gβγ or Mek*, respectively. (f) Immunoblot analysis for Thr188 phosphorylation of Erk2 in the presence of a Thr188-phosphorylated phosphopeptide, FLTEYVA-(p)T-RWYRAPE-amide, after incubation of Erk2 in the absence or presence of Gβγ or Mek*, respectively. (g) Comparison of amino acid sequences for mouse and human Erk1 and Erk2 demonstrates conservation of the region surrounding the three Erk2-phosphorylation sites Thr183, Tyr185 and Thr188 (SEQ ID NO: 2) (arrow).

FIG. 2 Hypertrophic stimuli induce a stable interaction of Gβγ with Raf1 and Erk1/2 and induce Thr188-phosphorylation of Erk1/2. (a, b) Immunoblot analyses for Gβ, Raf1 and Erk1/2 in neonatal rat cardiac myocyte lysates (NRCM) after immunoprecipitation (IP) using antibodies against Raf1 (anti-Raf1) or Erk1/2 (anti-Erk1/2), respectively. Co-immunoprecipitation of Gβ was observed only after treatment of NRCM with angiotensinII (Ang, 100 nM, 5 min) (a) but not after carbachol-treatment (CCH, 300 μM, 10 min) (c). (c, d) Immunoblot detection of Erk1/2-phosphorylation using pErk (Thr188)- and pErk(TEY)-specific antibodies in (e) adult cardiac myocytes after short-term stimulation and in (f) NRCM after long-term stimulation with carbachol (300 μM, 10 min or 36 h), angiotensinII (100 nM, 5 min or 24 h), neuregulin1-β1 (NRG, 20 ng ml$^{-1}$, 10 min or 36 h) and phenylephrine (PE, 35 μM, 5 min or 48 h). n=7-9; *, P<0.001 compared with total.

FIG. 3 Thr188-phosphorylation is critical for hypertrophy of neonatal rat cardiomyocytes (NRCMs) and cardiac hypertrophy. (a, b) [$^3$H]isoleucine-incorporation of NRCMs transfected with control plasmid (mock), wt-Erk2 (T188T), Erk2$^{T188S}$ or Erk2$^{T188D}$ incubated with or without angiotensinII (a) or carbachol (b). n=6-10; *, P<0.001 versus all other conditions. Inset, Erk2-immunoblot. Scale bar, 20 μm. (c) Heart-to-body weight ratio of WT and transgenic mice overexpressing Erk2$^{T188D}$, Erk2$^{T188S}$, wt-Erk2 or Erk2$^{T188A}$. n=10-14; *, P<0.001 versus WT (+TAC) and wt-Erk2 (+TAC). (d) Morphometric analysis of cardiomyocyte cross-sectional area without and after TAC. n=7-10 animals per group and 35-40 individual cells per animal were analyzed; *, P<0.001 versus WT (+TAC) and #, P<0.001 versus T188T (+TAC). (e) Quantification of interstitial fibrosis in the different transgenic mice without and after TAC using semiautomated image analysis. n=7-10 animals per group and four representative left ventricular sections per animal were analyzed; *, P<0.001 versus WT (+TAC) and #, P<0.001 versus T188T (+TAC). (f) Echocardiography of WT and transgenic mice overexpressing T188D, T188S, T188T or T188A 6 weeks after TAC (+TAC) versus age-matched controls (−TAC). Assessment of fractional shortening. n=10-14; *, P<0.001 versus WT (+TAC) and #, P<0.001 versus T188T (+TAC). (g, h) Dose-response curves for dp/dt$_{max}$ (g) and dp/dt$_{min}$ (h) after dobutamine infusion determined by measurements of left ventricular pressures in WT and Erk2$^{T188D}$-mice after TAC. n=8-12; P<0.05 versus WT. (i-k) Northern blot analyses of ANF (i, j) and BNP (k) relative to GAPDH-expression in total RNA obtained from hearts of wild-type mice, T188T, T188D, T188S or T188A transgenic mice without TAC (i) and 6 weeks after TAC (j, k), respectively. n=4-6; *, P<0.01 versus WT and #, P<0.01 versus T188T.

(l) Heart weight-to-tibia length ratios of WT and Erk2$^{T188S}$ without or with angiotensinII-treatment (left) and WT, Erk2$^{T188D}$ and wt-Erk2 mice without or with carbachol-treatment (right) for 14 days. n=5-10; *, P<0.001 versus WT and wt-Erk2. (m, n) Quantitative Northern blot analyses of ANF (m) and BNP (n) relative to GAPDH-expression in total RNA obtained from hearts of T188D overexpressing mice compared to control mice (WT) before and after application of CCH. n=4-6; *, P<0.05 versus WT (control).

FIG. 3.1 Neuregulin-induced cellular hypertrophy involves Gβγ. (a-c), Relative protein synthesis rates determined by [$^3$H]isoleucine incorporation (a, b) in neonatal rat cardiomyocytes (NRCMs) transfected with a control plasmid (mock) or GRK$^{495-689}$ (GRK2-CT) in the absence or presence of angiotensinII (Ang, 100 nM, 24 h) (a) or neuregulin1-β1 (NRG, 20 ng ml$^{-1}$, 24 h) (b). (c) Immunoblot analyses (IB) for Gβ, Raf1 and Erk1/2 in NRCMs after immunoprecipitation (IP) using antibodies against Raf1 (anti-Raf, upper panels) or Erk1/2 (anti-Erk1/2, lower panels) in the presence or absence of NRG (20 ng ml$^{-1}$, 10 min). (d) tyrosine phosphorylation of Gβ$_{q/11}$ detected with phosphoTyr-specific antibodies after immunoprecipitation of Gβ$_{q/11}$ from NRCMs in the absence or presence of NRG (20 ng ml$^{-1}$, 10 min). Comparable amounts of Gβ$_{q/11}$ were precipitated (lower panel). (e) Relative [$^3$H]isoleucine incorporation of NRCMs transfected with a control plasmid (mock) or with the phosphorylation-deficient mutant Gβ$_{11}$$^{Y356F}$ without or with NRG (20 ng ml$^{-1}$, 24 h). (f, g) Relative [$^3$H]isoleucine incorporation of NRCMs transfected with a control plasmid (mock), wild-type Erk2 (WT), Erk2$^{T188A}$ (T188A) (f) or Erk2$^{T188S}$ (T188S) (g) without or with NRG (20 ng ml$^{-1}$, 24 h). n=8-14; *, P<0.01 as indicated or versus all other conditions.

Figure 4:
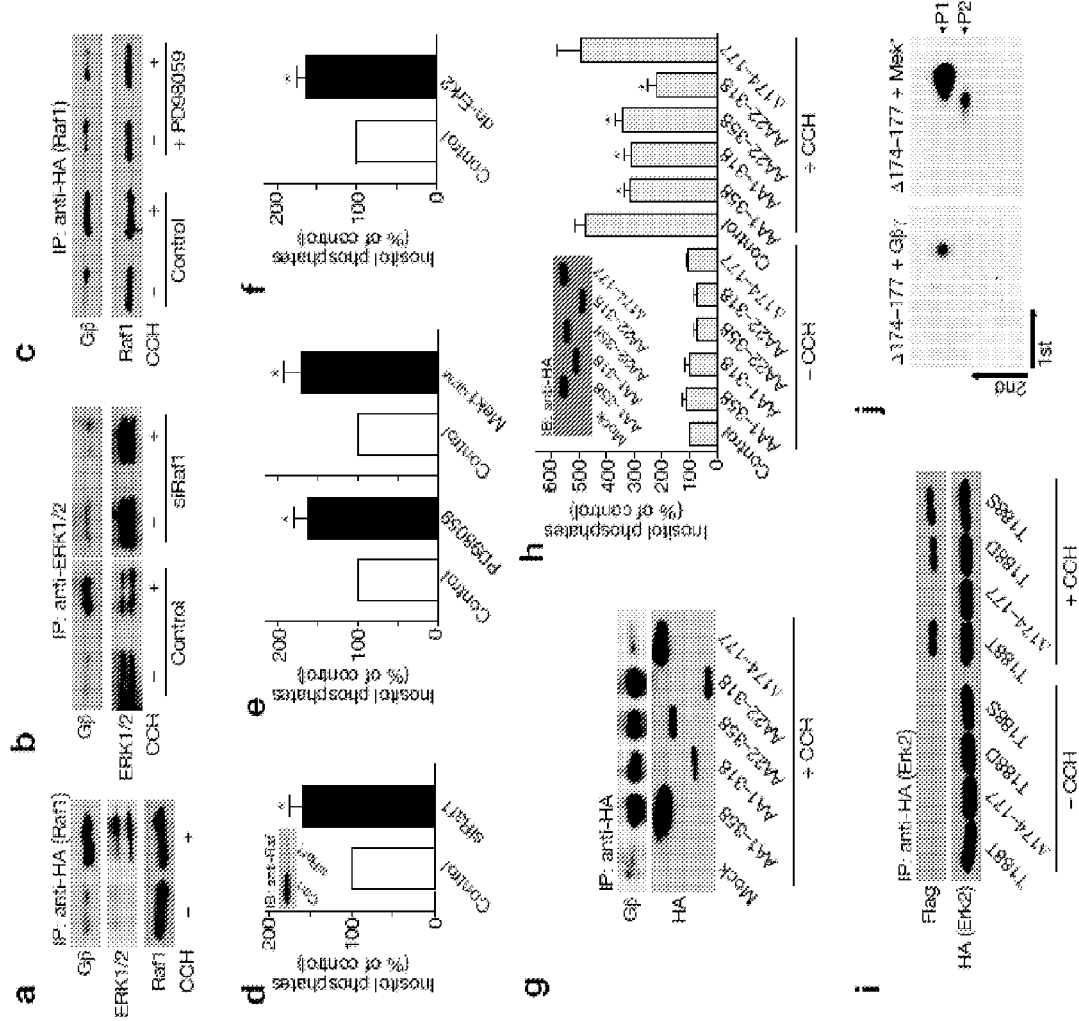
FIG. 4 shows that the activation of the entire MAPK-cascade is necessary for interaction of Gβγ with Erk1/2.

FIG. 4 Activation of the entire MAPK-cascade is necessary for interaction of Gβγ with Erk1/2. (a) HA-Raf1 (Raf1) immunoprecipitated (IP) with HA-specific antibodies (anti-HA) from HEK293 cell lysates forms a carbachol-induced (CCH, 5 min) complex with Erk1/2 and Gβ. (b) Gene silencing of Raf1 suppressed the carbachol-stimulated interaction of Erk1/2 with Gβ as assessed by co-immunoprecipitation with ERK1/2-specific antibodies (anti-ERK1/2). (c) Inhibition of Mek1/2-activity by PD98059 (50 μM) suppressed the carbachol-stimulated (CCH, 5 min) interaction of HA-Raf1 (Raf1) with Gβ as assessed by co-immunoprecipitation. (d-f) Downregulation of endogenous Raf1 by RNA interference (d), inhibition of endogenous Mek-activity by PD98059 (left panel) or by expression of the dominant-negative Mek1$^{K97M}$ (right panel) (e) or expression of the dominant-negative Erk2$^{T183A,Y185A}$ mutant (dn-Erk2) (f) enhanced carbachol-stimulated (50 μM, 15 min) inositol phosphate signaling compared to control cells. The decrease in Raf1 protein level by siRaf1 was controlled in immunoblot (IB) with Raf1-specific antibodies (d, inset, anti-Raf). (g, h) Interactions of HA-tagged wild-type Erk2 (AA1-358), truncated Erk2-mutants (AA1-318; AA22-358; AA22-318) and dimerization-deficient Erk2$^{\Delta174-177}$ with Gβγ as assessed by co-immunoprecipition (g) and carbachol-stimulated inositol phosphate signaling (h) in HEK293-cells. Inset, Erk2-immunoblot. (i) HA-tagged wt-Erk2 co-immunoprecipitates with Flag-tagged wt-Erk2 (T188T), Erk2$^{T188D}$, and Erk2$^{T188S}$ but not with Erk2$^{\Delta174-177}$ after carbachol-stimulation. (j) Two-dimensional phosphopeptide mapping of Erk2$^{\Delta174-177}$ after incubation with either Gβγ or Mek*. Phosphopeptides resulting from trypsin digestion of Erk2$^{\Delta174-177}$ are designated P1 and P2. n=3-10; *, P<0.01 versus respective controls.

FIG. 5 Thr188-phosphorylation promotes nuclear localization of Erk1/2. (a, b) Immunoblot analyses of heart lysates of wild-type mice (WT) and Erk2$^{T188}$-transgenic mouse lines for phosphorylation of the nuclear Erk1/2-targets Elk1, MSK1, cMyc (a), and of cytosolic p90RSK and p70S6k (b) after 6 weeks of TAC compared to age-matched WT without TAC. (c) Ratios of nuclear to cytosolic distribution of YFP-tagged wt-Erk2 (T188T), Erk2$^{T188D}$ and Erk2$^{T188S}$ without and with carbachol (CCH)-stimulation. COS7-cells were co-transfected with either $M_1$-receptors ($G_q$-coupled, left panel) or $M_2$-receptors ($G_E$-coupled, right panel). Representative cells transfected with the YFP-Erk2 constructs (left panels) and with $M_2$-receptors are shown without and with carbachol-stimulation. n=7-39; *, P<0.001. (d) Localization of Erk2 in heart sections of T188D, T188T and T188A transgenic mice before and 6 weeks after TAC using Erk2-specific antibodies followed by DAB-staining. Some cardiomyocyte nuclei are marked with arrowheads. (e) Immunohistochemical localization of Thr188-(pErk(Thr188), upper panels) and classically (pErk(TEY), lower panels) phosphorylated Erk1/2. Some cardiomyocyte nuclei are marked with arrowheads. Scale bars, 20 μm.

Figure 6:
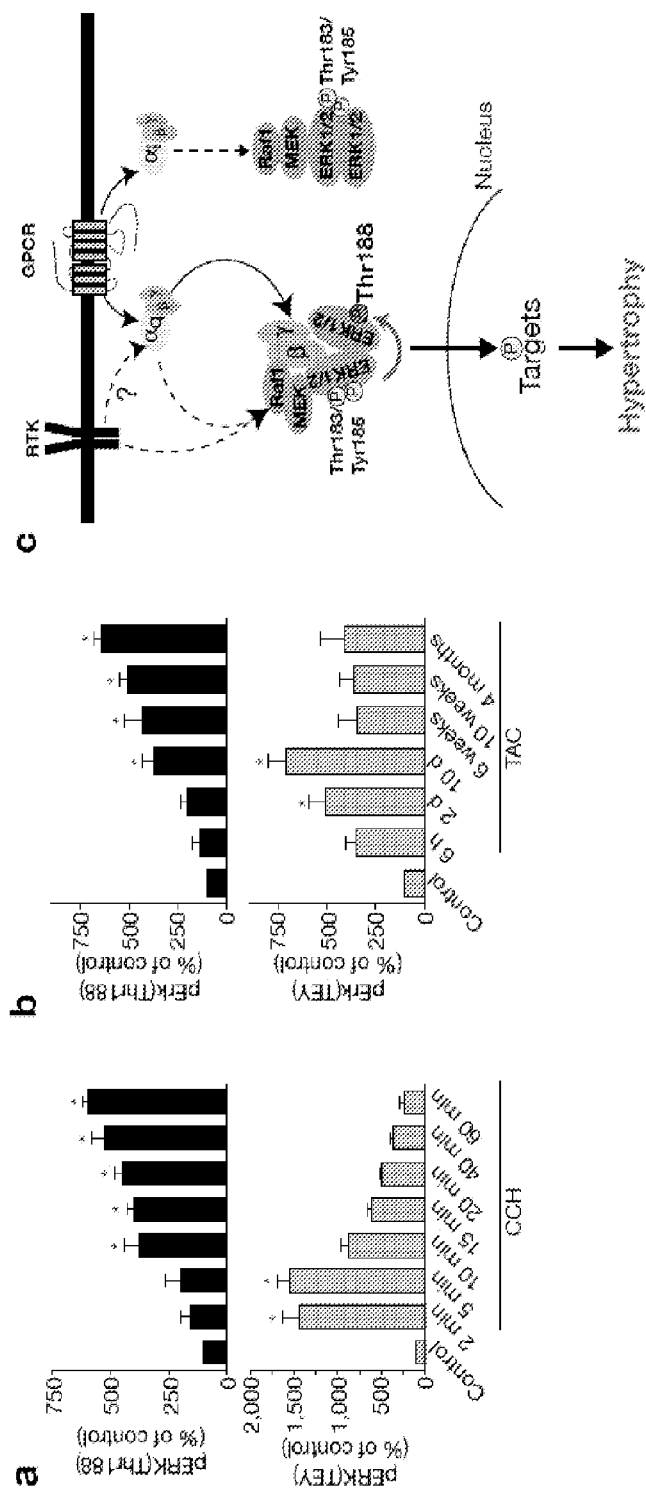
FIG. 6 shows Time courses and a mechanistic model for differential activation of the MAPK-cascade.

FIG. 6 Time courses and mechanistic model for differential activation of the MAPK-cascade. (a, b) Time-courses of Thr188 (pErk(Thr188)) versus classical (pErk(TEY)) Erk1/2 phosphorylation. HEK293-cells were transfected with HA-tagged Erk2 and stimulated with carbachol (CCH, 100 μM) (a); wild-type mice were subjected to TAC (b). n=3-10; *, P<0.05. (c) Activation of the MAPK-cascade induces phosphorylation of ERK1/2 within the TEY-motif. Subsequent dimerization of ERK1/2 in conjunction with a Gβγ-releasing stimulus (specifically activation of $G_q$-coupled receptors) leads to direct interaction of Gβγ with ERK1/2 and causes intermolecular autophosphorylation of ERK1/2 at Thr188. Phosphorylation of Thr188 stimulates nuclear localization of ERK1/2, nuclear ERK1/2-target phosphorylation and ERK1/2-mediated hypertrophy. Activation of the MAPK cascade by $G_i$-coupled receptors does not lead to direct Gβγ-binding with ERK1/2 and, therefore, does not induce Thr188-phosphorylation.

FIG. 7 (a) Western blot analysis of ERK1/2-phosphorylation at Thr188 (pERK(Thr188)) and the canonical sites (pERK(TEY)) using septal samples from patients with aortic stenosis (AS1-4; aortic stenosis) and myocardial control tissue (c1-4; control). (b) Quantification of Western blots shown in (a). The ratio of the pERK(Thr188) and pERK(TEY) to the ERK1/2 signal in the immunoblots was calculated for each individual and is quantified in the graphs (n=4 individuals per group; *P<0.006).

FIG. 8 The tissue analyzed for phosphoERK(TEY) and for pERK(Thr188) were derived from different cancers as follows: 3: oncozytoma, 4: metastasis of an intestinal adenocarcinoma, 5: colorectal adenocarcinoma (moderately differentiated G2, pN0), 8: uterine endometrioid carcinoma, 10: colon adenocarcinoma (moderately differentiated G2, pN1), 12: lung adenocarcinoma (moderately differentiated G2, pNx), 15: basal lung squamous cell carcinoma, G3, pN2, 16: lung adenocarcinoma (moderately differentiated G3, nN2), 17: small cell lung carcinoma; Westernblot was performed on all samples as described, with detection of total Erk as control.

REFERENCES

1. Bogoyevitch, M. A. & Sudgen, P. H. The role of protein kinases in adaptional growth of the heart. *Int. J. Cell. Biol.* 28, 1-12 (1996).
2. Brown, J. H., et al. Pathways and roadblocks in muscarinic receptor-mediated growth regulation. *Life Sci.* 60, 1077-1084 (1997).
3. Brunet, A. et al. Nuclear translocation of p42/p44 mitogen-activated protein kinase is required for growth factor-induced gene expression and cell cycle entry. *EMBO J.* 18, 664-674 (1999).
4. Garrington, T. P. & Johnson, G. L. Organization and regulation of mitogen-activated protein kinase signaling pathways. *Curr. Opin. Cell. Biol.* 11, 211-218 (1999).
5. Khokhlatchev, A. V. et al. Phosphorylation of the MAP kinase ERK2 promotes its homodimerization and nuclear translocation. *Cell* 93, 605-615 (1998).
6. Lorenz, K., Lohse, M. J. & Quitterer, U. Protein kinase C switches the Raf kinase inhibitor from Raf-1 to GRK-2. *Nature* 426, 574-579 (2003).
7. Mansour, S. J. et. al. Transformation of mammalian cells by constitutively active MAP kinase kinase. *Science* 265, 966-970 (1994).
8. Muslin, A. J. Role of Raf proteins in cardiac hypertrophy and cardiomyocyte survival. *Trends Cardiovasc. Med.* 15, 225-229 (2005).
9. Slupsky, J. R. et al. Binding of Gβγ subunits to cRaf1 down regulates G-protein-coupled receptor signalling. *Curr. Biol.* 9, 971-974 (1999).
10. Sugden, P. H. & Clerk, A. Cellular mechanisms of cardiac hypertrophy. *J. Mol. Med.* 76, 725-746 (1998).

The invention claimed is:

1. A purified phospho-specific antibody for Erk1/2 raised against a peptide consisting of SEQ ID NO: 1 wherein the Thr at position 8 of the sequence is phosphorylated, said antibody is specific to the peptide and does not cross-react with Erk phosphorylated at Thr183/Thr185.

2. The purified antibody of claim 1, wherein the antibody is monoclonal or polyclonal.

3. The purified antibody of claim 1, wherein the antibody binds to a peptide having SEQ ID NO: 1 with the Thr at position 8 being phosphorylated.

4. The purified antibody of claim 3, wherein the phosphorylated Thr is Thr$^{208}$ of Erk1 or Thr$^{188}$ of Erk2.

5. A composition which comprises the antibody of claim 1 which may be supplemented with the peptide of SEQ ID NO: 1.

6. An in vitro method for determining the presence of phosphorylated Erk1 and/or Erk2 (Erk1/2) in a sample, which comprises the steps of
   a) providing the antibody according to claim 1,
   b) incubating the sample with the antibody in vitro,
   c) detecting the antibody bound to the sample,
wherein binding of the antibody to the sample indicates the presence of phosphorylated Erk1/2 in the sample or the amount of antibody bound to the sample indicates the amount of Erk1/2 present in the sample.

7. The method of claim 6, wherein the sample is derived from a patient, preferably from a patient suffering from heart disease or cancer.

8. A method for producing an antibody according to claim 1, which comprises the steps of
   a) providing a peptide of SEQ ID NO: 1 in which the Thr at position 8 is phosphorylated, b) producing an antiserum against the peptide,
c) subjecting the antiserum to the peptide for isolating the antibody.

9. The method of claim 8, which further comprises the step of
d) supplementing the antibody with the peptide of SEQ ID NO: 1.

10. A kit for determining the presence of phosphorylated Erk1/2 in a sample, comprising the antibody according to claim 3.

11. An assay for diagnosing a heart disease, which comprises using the antibody according to claim 3 to detect the presence of the phosphorylated Thr at position 8, wherein the phosphorylated Thr indicates a heart disease, preferably cardiac hypertrophy.

12. An assay for detecting the presence and/or the amount of phosphorylated Erk1/2 in a sample which comprises contacting the sample with the antibody according to claim 3.

13. An assay for analyzing the hypertrophic stimulus of a patient or detecting Erk1/2 signalling activity in tissue, which comprises contacting the antibody according to claim 3 with a sample from the patient or the tissue.

14. A phospho-specific antibody for Erk1/2, obtained from a hybridoma, specific to a peptide consisting of SEQ ID NO: 1 wherein the Thr at position 8 of the sequence is phosphorylated, said antibody is specific to the peptide and does not cross-react with Erk phosphorylated at Thr183/Tyr 185.

* * * * *

SEQUENCE LISTING

<160> NUMBER OF SEQ ID NOS: 16

<210> SEQ ID NO 1
<211> LENGTH: 15
<212> TYPE: PRT
<213> ORGANISM: Artificial Sequence
<220> FEATURE:
<223> OTHER INFORMATION: Peptide sequence derived from human or mouse Erk.

<400> SEQUENCE: 1

Phe Leu Thr Glu Tyr Val Ala Thr Arg Trp Tyr Arg Ala Pro Glu
1               5                   10                  15

<210> SEQ ID NO 2
<211> LENGTH: 24

```
<212> TYPE: PRT
<213> ORGANISM: Artificial Sequence
<220> FEATURE:
<223> OTHER INFORMATION: Peptide sequence derived from human or mouse
      Erk.

<400> SEQUENCE: 2

His Asp His Thr Gly Phe Leu Thr Glu Tyr Val Ala Thr Arg Trp Tyr
1               5                   10                  15

Arg Ala Pro Glu Ile Met Leu Asn
            20

<210> SEQ ID NO 3
<211> LENGTH: 48
<212> TYPE: DNA
<213> ORGANISM: Artificial Sequence
<220> FEATURE:
<223> OTHER INFORMATION: DNA sequence derived from human or mouse Erk.

<400> SEQUENCE: 3
tttctgaccg aatatgtggc gacccgctgg tatcgcgcgc cggaataa                 48

<210> SEQ ID NO 4
<211> LENGTH: 15
<212> TYPE: PRT
<213> ORGANISM: Artificial Sequence
<220> FEATURE:
<223> OTHER INFORMATION: Peptide sequence derived from human or mouse
      Erk.

<400> SEQUENCE: 4

Phe Leu Thr Glu Tyr Val Ala Asp Arg Trp Tyr Arg Ala Pro Glu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Peptide sequence derived from human or mouse
      Erk.

<400> SEQUENCE: 5

Phe Leu Thr Glu Tyr Val Ala Ser Arg Trp Tyr Arg Ala Pro Glu
1               5                   10                  15

<210> SEQ ID NO 6
<211> LENGTH: 15
<212> TYPE: PRT
<213> ORGANISM: Artificial Sequence
<220> FEATURE:
<223> OTHER INFORMATION: Peptide sequence derived from human or mouse
      Erk.

<400> SEQUENCE: 6

Phe Leu Thr Glu Tyr Val Ala Ala Arg Trp Tyr Arg Ala Pro Glu
1               5                   10                  15

<210> SEQ ID NO 7
<211> LENGTH: 380
<212> TYPE: PRT
<213> ORGANISM: Mus musculus

<400> SEQUENCE: 7

Met Ala Ala Ala Ala Ala Ala Pro Gly Gly Gly Gly Gly Glu Pro Arg
1               5                   10                  15
```

Gly Thr Ala Gly Val Pro Val Pro Gly Glu Val Glu Val
                20              25              30

Lys Gly Gln Pro Phe Asp Val Gly Pro Arg Tyr Thr Gln Leu Gln Tyr
            35                  40                  45

Ile Gly Glu Gly Ala Tyr Gly Met Val Ser Ser Ala Tyr Asp His Val
 50                  55                  60

Arg Lys Thr Arg Val Ala Ile Lys Lys Ile Ser Pro Phe Glu His Gln
 65                  70                  75                  80

Thr Tyr Cys Gln Arg Thr Leu Arg Glu Ile Gln Ile Leu Leu Arg Phe
                85                  90                  95

Arg His Glu Asn Val Ile Gly Ile Arg Asp Ile Leu Arg Ala Pro Thr
            100                 105                 110

Leu Glu Ala Met Arg Asp Val Tyr Ile Val Gln Asp Leu Met Glu Thr
        115                 120                 125

Asp Leu Tyr Lys Leu Leu Lys Ser Gln Gln Leu Ser Asn Asp His Ile
130                 135                 140

Cys Tyr Phe Leu Tyr Gln Ile Leu Arg Gly Leu Lys Tyr Ile His Ser
145                 150                 155                 160

Ala Asn Val Leu His Arg Asp Leu Lys Pro Ser Asn Leu Leu Ile Asn
                165                 170                 175

Thr Thr Cys Asp Leu Lys Ile Cys Asp Phe Gly Leu Ala Arg Ile Ala
            180                 185                 190

Asp Pro Glu His Asp His Thr Gly Phe Leu Thr Glu Tyr Val Ala Thr
        195                 200                 205

Arg Trp Tyr Arg Ala Pro Glu Ile Met Leu Asn Ser Lys Gly Tyr Thr
210                 215                 220

Lys Ser Ile Asp Ile Trp Ser Val Gly Cys Ile Leu Ala Glu Met Leu
225                 230                 235                 240

Ser Asn Arg Pro Ile Phe Pro Gly Lys His Tyr Leu Asp Gln Leu Asn
                245                 250                 255

His Ile Leu Gly Ile Leu Gly Ser Pro Ser Gln Glu Asp Leu Asn Cys
            260                 265                 270

Ile Ile Asn Met Lys Ala Arg Asn Tyr Leu Gln Ser Leu Pro Ser Lys
        275                 280                 285

Thr Lys Val Ala Trp Ala Lys Leu Phe Pro Lys Ser Asp Ser Lys Ala
290                 295                 300

Leu Asp Leu Leu Asp Arg Met Leu Thr Phe Asn Pro Asn Lys Arg Ile
305                 310                 315                 320

Thr Val Glu Glu Ala Leu Ala His Pro Tyr Leu Glu Gln Tyr Tyr Asp
                325                 330                 335

Pro Thr Asp Glu Pro Val Ala Glu Glu Pro Phe Thr Phe Asp Met Glu
            340                 345                 350

Leu Asp Asp Leu Pro Lys Glu Arg Leu Lys Glu Leu Ile Phe Gln Glu
        355                 360                 365

Thr Ala Arg Phe Gln Pro Gly Ala Pro Glu Gly Pro
370                 375                 380

<210> SEQ ID NO 8
<211> LENGTH: 358
<212> TYPE: PRT
<213> ORGANISM: Mus musculus

<400> SEQUENCE: 8

Met Ala Ala Ala Ala Ala Gly Pro Glu Met Val Arg Gly Gln Val
 1               5                  10                  15

Phe Asp Val Gly Pro Arg Tyr Thr Asn Leu Ser Tyr Ile Gly Glu Gly
            20                  25                  30

Ala Tyr Gly Met Val Cys Ser Ala Tyr Asp Asn Leu Asn Lys Val Arg
            35                  40                  45

Val Ala Ile Lys Lys Ile Ser Pro Phe Glu His Gln Thr Tyr Cys Gln
 50                  55                  60

Arg Thr Leu Arg Glu Ile Lys Ile Leu Leu Arg Phe Arg His Glu Asn
 65                  70                  75                  80

Ile Ile Gly Ile Asn Asp Ile Ile Arg Ala Pro Thr Ile Glu Gln Met
                 85                  90                  95

Lys Asp Val Tyr Ile Val Gln Asp Leu Met Glu Thr Asp Leu Tyr Lys
            100                 105                 110

Leu Leu Lys Thr Gln His Leu Ser Asn Asp His Ile Cys Tyr Phe Leu
            115                 120                 125

Tyr Gln Ile Leu Arg Gly Leu Lys Tyr Ile His Ser Ala Asn Val Leu
130                 135                 140

His Arg Asp Leu Lys Pro Ser Asn Leu Leu Leu Asn Thr Thr Cys Asp
145                 150                 155                 160

Leu Lys Ile Cys Asp Phe Gly Leu Ala Arg Val Ala Asp Pro Asp His
                165                 170                 175

Asp His Thr Gly Phe Leu Thr Glu Tyr Val Ala Thr Arg Trp Tyr Arg
            180                 185                 190

Ala Pro Glu Ile Met Leu Asn Ser Lys Gly Tyr Thr Lys Ser Ile Asp
            195                 200                 205

Ile Trp Ser Val Gly Cys Ile Leu Ala Glu Met Leu Ser Asn Arg Pro
210                 215                 220

Ile Phe Pro Gly Lys His Tyr Leu Asp Gln Leu Asn His Ile Leu Gly
225                 230                 235                 240

Ile Leu Gly Ser Pro Ser Gln Glu Asp Leu Asn Cys Ile Ile Asn Leu
                245                 250                 255

Lys Ala Arg Asn Tyr Leu Leu Ser Leu Pro His Lys Asn Lys Val Pro
            260                 265                 270

Trp Asn Arg Leu Phe Pro Asn Ala Asp Ser Lys Ala Leu Asp Leu Leu
            275                 280                 285

Asp Lys Met Leu Thr Phe Asn Pro His Lys Arg Ile Glu Val Glu Gln
290                 295                 300

Ala Leu Ala His Pro Tyr Leu Glu Gln Tyr Tyr Asp Pro Ser Asp Glu
305                 310                 315                 320

Pro Ile Ala Glu Ala Pro Phe Lys Phe Asp Met Glu Leu Asp Asp Leu
                325                 330                 335

Pro Lys Glu Lys Leu Lys Glu Leu Ile Phe Glu Glu Thr Ala Arg Phe
            340                 345                 350

Gln Pro Gly Tyr Arg Ser
            355

<210> SEQ ID NO 9
<211> LENGTH: 379
<212> TYPE: PRT
<213> ORGANISM: Homo sapiens

<400> SEQUENCE: 9

Met Ala Ala Ala Ala Gln Gly Gly Gly Gly Gly Glu Pro Arg Arg
1               5                   10                  15

Thr Glu Gly Val Gly Pro Gly Val Pro Gly Glu Val Glu Met Val Lys

```
            20                  25                  30
Gly Gln Pro Phe Asp Val Gly Pro Arg Tyr Thr Gln Leu Gln Tyr Ile
         35                  40                  45
Gly Glu Gly Ala Tyr Gly Met Val Ser Ser Ala Tyr Asp His Val Arg
 50                  55                  60
Lys Thr Arg Val Ala Ile Lys Lys Ile Ser Pro Phe Glu His Gln Thr
 65                  70                  75                  80
Tyr Cys Gln Arg Thr Leu Arg Glu Ile Gln Ile Leu Leu Arg Phe Arg
                 85                  90                  95
His Glu Asn Val Ile Gly Ile Arg Asp Ile Leu Arg Ala Ser Thr Leu
            100                 105                 110
Glu Ala Met Arg Asp Val Tyr Ile Val Gln Asp Leu Met Glu Thr Asp
            115                 120                 125
Leu Tyr Lys Leu Leu Lys Ser Gln Gln Leu Ser Asn Asp His Ile Cys
         130                 135                 140
Tyr Phe Leu Tyr Gln Ile Leu Arg Gly Leu Lys Tyr Ile His Ser Ala
145                 150                 155                 160
Asn Val Leu His Arg Asp Leu Lys Pro Ser Asn Leu Leu Ile Asn Thr
                165                 170                 175
Thr Cys Asp Leu Lys Ile Cys Asp Phe Gly Leu Ala Arg Ile Ala Asp
            180                 185                 190
Pro Glu His Asp His Thr Gly Phe Leu Thr Glu Tyr Val Ala Thr Arg
            195                 200                 205
Trp Tyr Arg Ala Pro Glu Ile Met Leu Asn Ser Lys Gly Tyr Thr Lys
210                 215                 220
Ser Ile Asp Ile Trp Ser Val Gly Cys Ile Leu Ala Glu Met Leu Ser
225                 230                 235                 240
Asn Arg Pro Ile Phe Pro Gly Lys His Tyr Leu Asp Gln Leu Asn His
                245                 250                 255
Ile Leu Gly Ile Leu Gly Ser Pro Ser Gln Glu Asp Leu Asn Cys Ile
            260                 265                 270
Ile Asn Met Lys Ala Arg Asn Tyr Leu Gln Ser Leu Pro Ser Lys Thr
         275                 280                 285
Lys Val Ala Trp Ala Lys Leu Phe Pro Lys Ser Asp Ser Lys Ala Leu
         290                 295                 300
Asp Leu Leu Asp Arg Met Leu Thr Phe Asn Pro Asn Lys Arg Ile Thr
305                 310                 315                 320
Val Glu Glu Ala Leu Ala His Pro Tyr Leu Glu Gln Tyr Tyr Asp Pro
                325                 330                 335
Thr Asp Glu Pro Val Ala Glu Pro Phe Thr Phe Ala Met Glu Leu
            340                 345                 350
Asp Asp Leu Pro Lys Glu Arg Leu Lys Glu Leu Ile Phe Gln Glu Thr
         355                 360                 365
Ala Arg Phe Gln Pro Gly Val Leu Glu Ala Pro
         370                 375

<210> SEQ ID NO 10
<211> LENGTH: 360
<212> TYPE: PRT
<213> ORGANISM: Homo sapiens

<400> SEQUENCE: 10

Met Ala Ala Ala Ala Ala Gly Ala Gly Pro Glu Met Val Arg Gly
 1               5                  10                  15
```

```
Gln Val Phe Asp Val Gly Pro Arg Tyr Thr Asn Leu Ser Tyr Ile Gly
             20                  25                  30
Glu Gly Ala Tyr Gly Met Val Cys Ser Ala Tyr Asp Asn Val Asn Lys
         35                  40                  45
Val Arg Val Ala Ile Lys Lys Ile Ser Pro Phe Glu His Gln Thr Tyr
     50                  55                  60
Cys Gln Arg Thr Leu Arg Glu Ile Lys Ile Leu Leu Arg Phe Arg His
 65                  70                  75                  80
Glu Asn Ile Ile Gly Ile Asn Asp Ile Ile Arg Ala Pro Thr Ile Glu
                 85                  90                  95
Gln Met Lys Asp Val Tyr Ile Val Gln Asp Leu Met Glu Thr Asp Leu
            100                 105                 110
Tyr Lys Leu Leu Lys Thr Gln His Leu Ser Asn Asp His Ile Cys Tyr
        115                 120                 125
Phe Leu Tyr Gln Ile Leu Arg Gly Leu Lys Tyr Ile His Ser Ala Asn
130                 135                 140
Val Leu His Arg Asp Leu Lys Pro Ser Asn Leu Leu Leu Asn Thr Thr
145                 150                 155                 160
Cys Asp Leu Lys Ile Cys Asp Phe Gly Leu Ala Arg Val Ala Asp Pro
                165                 170                 175
Asp His Asp His Thr Gly Phe Leu Thr Glu Tyr Val Ala Thr Arg Trp
            180                 185                 190
Tyr Arg Ala Pro Glu Ile Met Leu Asn Ser Lys Gly Tyr Thr Lys Ser
        195                 200                 205
Ile Asp Ile Trp Ser Val Gly Cys Ile Leu Ala Glu Met Leu Ser Asn
210                 215                 220
Arg Pro Ile Phe Pro Gly Lys His Tyr Leu Asp Gln Leu Asn His Ile
225                 230                 235                 240
Leu Gly Ile Leu Gly Ser Pro Ser Gln Glu Asp Leu Asn Cys Ile Ile
                245                 250                 255
Asn Leu Lys Ala Arg Asn Tyr Leu Leu Ser Leu Pro His Lys Asn Lys
            260                 265                 270
Val Pro Trp Asn Arg Leu Phe Pro Asn Ala Asp Ser Lys Ala Leu Asp
        275                 280                 285
Leu Leu Asp Lys Met Leu Thr Phe Asn Pro His Lys Arg Ile Glu Val
290                 295                 300
Glu Gln Ala Leu Ala His Pro Tyr Leu Glu Gln Tyr Tyr Asp Pro Ser
305                 310                 315                 320
Asp Glu Pro Ile Ala Glu Ala Pro Phe Lys Phe Asp Met Glu Leu Asp
                325                 330                 335
Asp Leu Pro Lys Glu Lys Leu Lys Glu Leu Ile Phe Glu Glu Thr Ala
            340                 345                 350
Arg Phe Gln Pro Gly Tyr Arg Ser
        355                 360

<210> SEQ ID NO 11
<211> LENGTH: 22
<212> TYPE: DNA
<213> ORGANISM: Artificial Sequence
<220> FEATURE:
<223> OTHER INFORMATION: Synthesized GAPDH forward primer.

<400> SEQUENCE: 11
cgagaccccg ctaacatcaa at                                          22
```

```
<210> SEQ ID NO 12
<211> LENGTH: 19
<212> TYPE: DNA
<213> ORGANISM: Artificial Sequence
<220> FEATURE:
<223> OTHER INFORMATION: Synthesized GAPDH reverse primer.

<400> SEQUENCE: 12
gcagccccac agccatcat                                                19

<210> SEQ ID NO 13
<211> LENGTH: 17
<212> TYPE: DNA
<213> ORGANISM: Artificial Sequence
<220> FEATURE:
<223> OTHER INFORMATION: Synthesized BNP forward primer.

<400> SEQUENCE: 13
tggggaggcg agacaag                                                  17

<210> SEQ ID NO 14
<211> LENGTH: 17
<212> TYPE: DNA
<213> ORGANISM: Artificial Sequence
<220> FEATURE:
<223> OTHER INFORMATION: Synthesized BNP reverse primer.

<400> SEQUENCE: 14
agcccaaacg actgacg                                                  17

<210> SEQ ID NO 15
<211> LENGTH: 24
<212> TYPE: DNA
<213> ORGANISM: Artificial Sequence
<220> FEATURE:
<223> OTHER INFORMATION: Synthesized ANP forward primer.

<400> SEQUENCE: 15
accctgggct tcttcctcgt cttg                                          24

<210> SEQ ID NO 16
<211> LENGTH: 24
<212> TYPE: DNA
<213> ORGANISM: Artificial Sequence
<220> FEATURE:
<223> OTHER INFORMATION: Synthesized ANP reverse primer.

<400> SEQUENCE: 16
cctttccctc cttggctgtt atct                                          24
```